US012570713B2

(12) United States Patent
Li et al.

(10) Patent No.: US 12,570,713 B2
(45) Date of Patent: Mar. 10, 2026

(54) HIGH-AFFINITY TCR FOR RECOGNIZING AFP ANTIGEN

(71) Applicant: XLifeSc, Ltd., Guangzhou (CN)

(72) Inventors: Yi Li, Guangzhou (CN); Xiaolin Li, Guangzhou (CN)

(73) Assignee: XLifeSc, Ltd., Zhuhai (CN)

( * ) Notice: Subject to any disclaimer, the term of this patent is extended or adjusted under 35 U.S.C. 154(b) by 1129 days.

(21) Appl. No.: 17/437,212

(22) PCT Filed: Mar. 6, 2020

(86) PCT No.: PCT/CN2020/078271
§ 371 (c)(1),
(2) Date: Sep. 8, 2021

(87) PCT Pub. No.: WO2020/182082
PCT Pub. Date: Sep. 17, 2020

(65) Prior Publication Data
US 2022/0169697 A1     Jun. 2, 2022

(30) Foreign Application Priority Data

Mar. 8, 2019    (CN) .......................... 201910176833.6

(51) Int. Cl.
| | |
|---|---|
| *A61K 40/11* | (2025.01) |
| *A61K 38/00* | (2006.01) |
| *A61K 40/32* | (2025.01) |
| *A61K 40/42* | (2025.01) |
| *A61P 35/00* | (2006.01) |
| *C07K 14/725* | (2006.01) |
| *C12N 1/20* | (2006.01) |
| *C12N 5/0783* | (2010.01) |
| *C12N 15/62* | (2006.01) |
| *C12N 15/70* | (2006.01) |

(52) U.S. Cl.
CPC .......... *C07K 14/7051* (2013.01); *A61K 40/11* (2025.01); *A61K 40/32* (2025.01); *A61K 40/4265* (2025.01); *A61P 35/00* (2018.01); *C12N 1/20* (2013.01); *C12N 5/0636* (2013.01); *C12N 15/625* (2013.01); *C12N 15/70* (2013.01); *A61K 38/00* (2013.01); *A61K 2239/31* (2023.05); *A61K 2239/38* (2023.05); *A61K 2239/53* (2023.05); *C12N 2510/00* (2013.01); *C12N 2800/101* (2013.01)

(58) Field of Classification Search
CPC ............ C07K 14/7051; C07K 2317/31; C07K 2317/73; C07K 2319/00; C07K 16/2809; C07K 2317/32; C07K 2317/34; C07K 2317/622; C07K 2317/92; C07K 16/18; C07K 16/2833; C07K 2317/565; A61K 40/11; A61K 40/32; A61K 40/4265; A61K 38/00; A61K 2239/31; A61K 2239/38; A61K 2239/53; A61K 2039/505;

A61P 35/00; C12N 1/20; C12N 5/0636; C12N 15/625; C12N 15/70; C12N 2510/00; C12N 2800/101
See application file for complete search history.

(56) References Cited

FOREIGN PATENT DOCUMENTS

| | | |
|---|---|---|
| CN | 104087592 A | 10/2014 |
| CN | 105408353 A | 3/2016 |
| CN | 105524884 A | 4/2016 |
| CN | 107106671 A | 8/2017 |
| JP | 2017081836 A | 5/2017 |
| WO | 2011140284 A2 | 11/2011 |
| WO | 2014206304 A1 | 12/2014 |
| WO | 2016070814 A1 | 5/2016 |
| WO | 2017089759 A1 | 6/2017 |
| WO | 2020024915 A1 | 2/2020 |

OTHER PUBLICATIONS

Card et al., A Soluble Single-Chain T-Cell Receptor IL-2 Fusion Protein Retains MHC-Restricted Peptide Specificity and IL-2 Bioactivity, Cancer Immunology, Immunotherapy, 2004, 53(4):345-357.
Chaudhary et al., A Recombinant Immunotoxin Consisting of Two Antibody Variable Domains Fused to Pseudomonas Exotoxin, Nature, 1989, 339(6223):394-397.
Epel et al., A Functional Recombinant Single-Chain T Cell Receptor Fragment Capable of Selectively Targeting Antigen-Presenting Cells, Cancer Immunology, Immunotherapy, 2002, 51(10):565-573.
Gillies et al., Antibody-Targeted Interleukin 2 Stimulates T-cell Killing of Autologous Tumor Cells, Proc. Natl. Acad. Sci. USA, 1992, 89:1428-1432.
Halin et al., Synergistic Therapeutic Effects of a Tumor Targeting Antibody Fragment, Fused to Interleukin 12 and to Tumor Necrosis Factor α, Cancer Research, 2003, 63(12):3202-3210.
Huang et al., Cancer Cell Imaging and Photothermal Therapy in the Near-Infrared Region by Using Gold Nanorods, Journal of the American Chemical Society, 2006, 128(6):2115-2120.
Koppe et al., Antibody-Guided Radiation Therapy of Cancer, Cancer and Metastasis Reviews, 2005, 24:539-567.
Lapotko et al., Method of Laser Activated Nano-Thermolysis for Elimination of Tumor Cells, Cancer Letters, 2006, 239(1):36-45.
Li et al., Directed Evolution of Human T-Cell Receptors with Picomolar Affinities by Phage Display, Nature Biotechnology, 2005, 23(3):349-354.

(Continued)

*Primary Examiner* — Chun W Dahle
*Assistant Examiner* — James Lyle McLellan
(74) *Attorney, Agent, or Firm* — Quarles & Brady LLP

(57) ABSTRACT

Provided in the present invention is a T-cell receptor (TCR) having the characteristic of binding a FMNKFIYEI-HLA A0201 complex. The binding affinity of the TCR to the FMNKFIYEI-HLA A0201 complex is at least 5 times that of a wild-type TCR to the FMNKFIYEI-HLA A0201 complex. Further provided in the present invention is a fusion molecule of the TCR with a therapeutic agent. The TCR may be used alone or in combination with the therapeutic agent, so as to target a tumor cell presenting the FMNKFIYEI-HLA A0201 complex.

19 Claims, 7 Drawing Sheets

Specification includes a Sequence Listing.

(56)                  References Cited

OTHER PUBLICATIONS

Mamot et al., Epidermal Growth Factor Receptor-Targeted Immunoliposomes Significantly Enhance the Efficacy of Multiple Anticancer Drugs In Vivo, Cancer Research, 2005, 65(24):11631-11638.

Mosquera et al., In Vitro and In Vivo Characterization of a Novel Antibody-Like Single-Chain TCR Human IgG1 Fusion Protein, Journal of Immunology, 2005, 174(7):4381-4388.

Peng et al., Targeting Virus Entry and Membrane Fusion Through Specific Peptide/MHC Complexes Using a High-Affinity T-Cell Receptor, Gene Therapy, 2004, 11(15):1234-1239.

Robbins et al., Single and Dual Amino Acid Substitutions in TCR CDRs Can Enhance Antigen-Specific T Cell Functions, Journal of Immunology, 2008, 180(9):6116-6131.

Rosenberg et al., Adoptive Cell Transfer: A Clinical Path to Effective Cancer Immunotherapy, Nature Reviews Cancer, 2008, 8(4):299-308.

Zhu et al., Engineering High Affinity Humanized Anti-p185HER2/Anti-CD3 Bispecific F(ab') 2 for Efficient Lysis of o185HER2 Overexpressing Tumor Cells, International Journal of Cancer, 1995, 62(3):319-324.

PCT International Search Report and Written Opinion, PCT/CN2020/078271, Jun. 11, 2020, 19 pages.

The State Intellectual Property Office of People's Republic of China, First Office Action, Apr. 20, 2022, 10 pages.

Docta et al., Tuning T-Cell Receptor Affinity to Optimize Clinical Risk-Benefit When Targeting Alpha-Fetoprotein-Positive Liver Cancer, Hepatology, 2019, 69(5):2061-2075.

Dong et al., Prediction of HLA-A2-restricted CTL epitope derived from tumor antigens associated with hepatocellular carcinoma, J Fourth Mil Med Univ, 2003, 24(6):492-494.

Zhu et al., Identification of alpha-Fetoprotein-Specific T-Cell Receptors for Hepatocellular Carcinoma Immunotherapy, Hepatology, 2018, 68(2):574-589.

European Patent Office, Extended European Search Report, Application No. 20771141.7, Dec. 5, 2022, 12 pages.

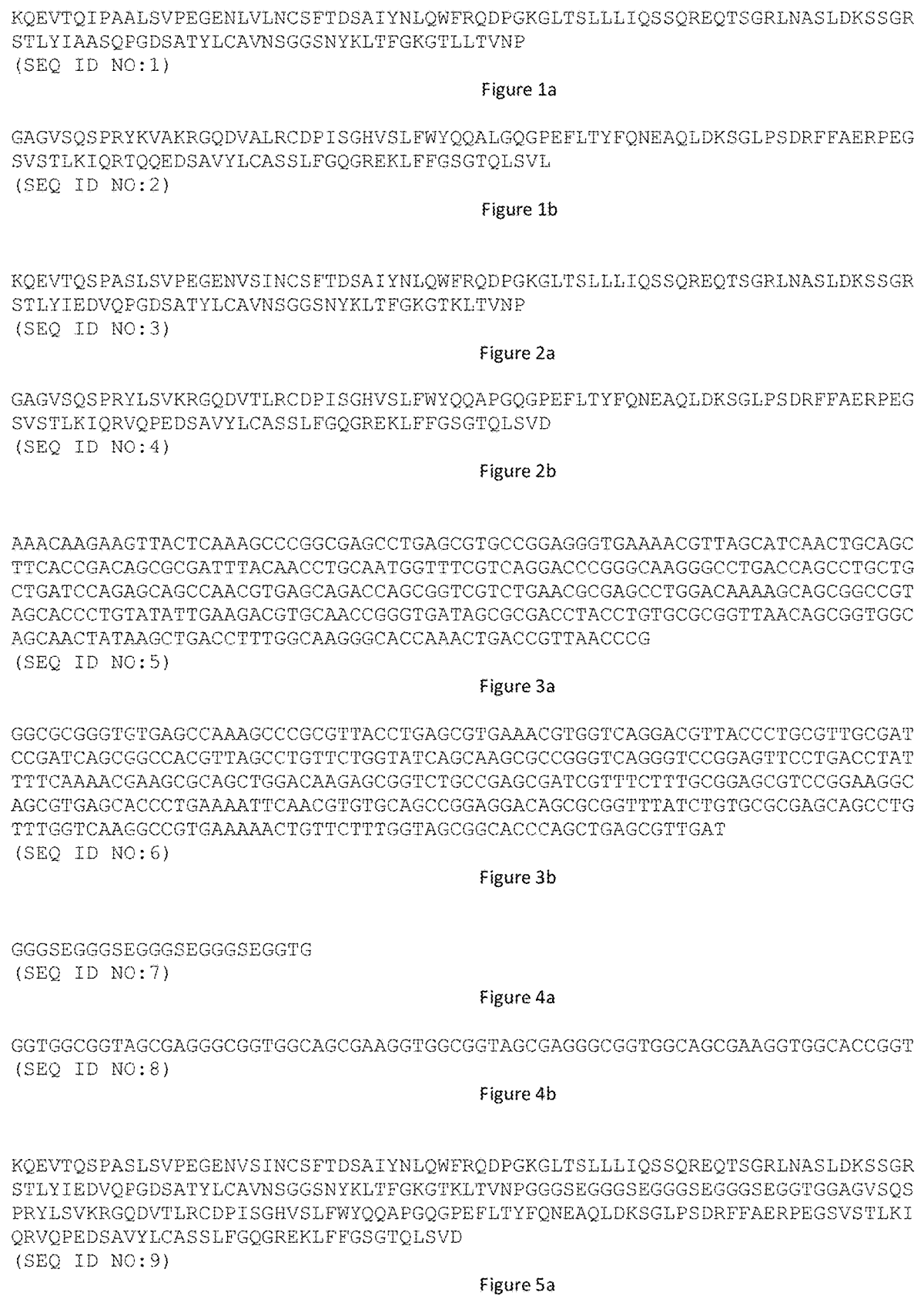

KQEVTQIPAALSVPEGENLVLNCSFTDSAIYNLQWFRQDPGKGLTSLLLIQSSQREQTSGRLNASLDKSSGR
STLYIAASQPGDSATYLCAVNSGGSNYKLTFGKGTLLTVNP
(SEQ ID NO:1)

Figure 1a

GAGVSQSPRYKVAKRGQDVALRCDPISGHVSLFWYQQALGQGPEFLTYFQNEAQLDKSGLPSDRFFAERPEG
SVSTLKIQRTQQEDSAVYLCASSLFGQGREKLFFGSGTQLSVL
(SEQ ID NO:2)

Figure 1b

KQEVTQSPASLSVPEGENVSINCSFTDSAIYNLQWFRQDPGKGLTSLLLIQSSQREQTSGRLNASLDKSSGR
STLYIEDVQPGDSATYLCAVNSGGSNYKLTFGKGTKLTVNP
(SEQ ID NO:3)

Figure 2a

GAGVSQSPRYLSVKRGQDVTLRCDPISGHVSLFWYQQAPGQGPEFLTYFQNEAQLDKSGLPSDRFFAERPEG
SVSTLKIQRVQPEDSAVYLCASSLFGQGREKLFFGSGTQLSVD
(SEQ ID NO:4)

Figure 2b

AAACAAGAAGTTACTCAAAGCCCGGCGAGCCTGAGCGTGCCGGAGGGTGAAAACGTTAGCATCAACTGCAGC
TTCACCGACAGCGCGATTTACAACCTGCAATGGTTTCGTCAGGACCCGGGCAAGGGCCTGACCAGCCTGCTG
CTGATCCAGAGCAGCCAACGTGAGCAGACCAGCGGTCGTCTGAACGCGAGCCTGGACAAAAGCAGCGGCCGT
AGCACCCTGTATATTGAAGACGTGCAACCGGGTGATAGCGCGACCTACCTGTGCGCGGTTAACAGCGGTGGC
AGCAACTATAAGCTGACCTTTGGCAAGGGCACCAAACTGACCGTTAACCCG
(SEQ ID NO:5)

Figure 3a

GGCGCGGGTGTGAGCCAAAGCCCGCGTTACCTGAGCGTGAAACGTGGTCAGGACGTTACCCTGCGTTGCGAT
CCGATCAGCGGCCACGTTAGCCTGTTCTGGTATCAGCAAGCGCCGGGTCAGGGTCCGGAGTTCCTGACCTAT
TTTCAAAACGAAGCGCAGCTGGACAAGAGCGGTCTGCCGAGCGATCGTTTCTTTGCGGAGCGTCCGGAAGGC
AGCGTGAGCACCCTGAAAATTCAACGTGTGCAGCCGGAGGACAGCGCGGTTTATCTGTGCGCGAGCAGCCTG
TTTGGTCAAGGCCGTGAAAAACTGTTCTTTGGTAGCGGCACCCAGCTGAGCGTTGAT
(SEQ ID NO:6)

Figure 3b

GGGSEGGGSEGGGSEGGGSEGGTG
(SEQ ID NO:7)

Figure 4a

GGTGGCGGTAGCGAGGGCGGTGGCAGCGAAGGTGGCGGTAGCGAGGGCGGTGGCAGCGAAGGTGGCACCGGT
(SEQ ID NO:8)

Figure 4b

KQEVTQSPASLSVPEGENVSINCSFTDSAIYNLQWFRQDPGKGLTSLLLIQSSQREQTSGRLNASLDKSSGR
STLYIEDVQPGDSATYLCAVNSGGSNYKLTFGKGTKLTVNPGGGSEGGGSEGGGSEGGGSEGGTGGAGVSQS
PRYLSVKRGQDVTLRCDPISGHVSLFWYQQAPGQGPEFLTYFQNEAQLDKSGLPSDRFFAERPEGSVSTLKI
QRVQPEDSAVYLCASSLFGQGREKLFFGSGTQLSVD
(SEQ ID NO:9)

Figure 5a

AAACAAGAAGTTACTCAAAGCCCGGCGAGCCTGAGCGTGCCGGAGGGTGAAAACGTTAGCATCAACTGCAGC
TTCACCGACAGCGCGATTTACAACCTGCAATGGTTTCGTCAGGACCCGGGCAAGGGCCTGACCAGCCTGCTG
CTGATCCAGAGCAGCCAACGTGAGCAGACCAGCGGTCGTCTGAACGCGAGCCTGGACAAAAGCAGCGGCCGT
AGCACCCTGTATATTGAAGACGTGCAACCGGGTGATAGCGCGACCTACCTGTGCGCGGTTAACAGCGGTGGC
AGCAACTATAAGCTGACCTTTGGCAAGGGCACCAAACTGACCGTTAACCCGGGTGGCGGTAGCGAGGGCGGT
GGCAGCGAAGGTGGCGGTAGCGAGGGCGGTGGCAGCGAAGGTGGCACCGGTGGCGCGGGTGTGAGCCAAAGC
CCGCGTTACCTGAGCGTGAAACGTGGTCAGGACGTTACCCTGCGTTGCGATCCGATCAGCGGCCACGTTAGC
CTGTTCTGGTATCAGCAAGCGCCGGGTCAGGGTCCGGAGTTCCTGACCTATTTTCAAAACGAAGCGCAGCTG
GACAAGAGCGGTCTGCCGAGCGATCGTTTCTTTGCGGAGCGTCCGGAAGGCAGCGTGAGCACCCTGAAAATT
CAACGTGTGCAGCCGGAGGACAGCGCGGTTTATCTGTGCGCGAGCAGCCTGTTTGGTCAAGGCCGTGAAAAA
CTGTTCTTTGGTAGCGGCACCCAGCTGAGCGTTGAT
(SEQ ID NO:10)

Figure 5b

KQEVTQIPAALSVPEGENLVLNCSFTDSAIYNLQWFRQDPGKGLTSLLLIQSSQREQTSGRLNASLDKSSGR
STLYIAASQPGDSATYLCAV<u>DSGG</u>SNYKLTFGKGTLLTVNP
(SEQ ID NO:11)

Figure 6a

KQEVTQIPAALSVPEGENLVLNCSFTDSAIYNLQWFRQDPGKGLTSLLLIQSSQREQTSGRLNASLDKSSGR
STLYIAASQPGDSATYLCAV<u>EDQG</u>SNYKLTFGKGTLLTVNP
(SEQ ID NO:12)

Figure 6b

KQEVTQIPAALSVPEGENLVLNCSFTDSAIYNLQWFRQDPGKGLTSLLLIQSSQREQTSGRLNASLDKSSGR
STLYIAASQPGDSATYLCAV<u>DGAD</u>SNYKLTFGKGTLLTVNP
(SEQ ID NO:13)

Figure 6c

KQEVTQIPAALSVPEGENLVLNCSFTDSAIYNLQWFRQDPGKGLTSLLLIQSSQREQTSGRLNASLDKSSGR
STLYIAASQPGDSATYLCAVNS<u>VRGG</u>YKLTFGKGTLLTVNP
(SEQ ID NO:14)

Figure 6d

KQEVTQIPAALSVPEGENLVLNCSFTDSAIYNLQWFRQDPGKGLTSLLLIQSSQREQTSGRLNASLDKSSGR
STLYIAASQPGDSATYLCAV<u>EGAR</u>SNYKLTFGKGTLLTVNP
(SEQ ID NO:15)

Figure 6e

KQEVTQIPAALSVPEGENLVLNCSFTDSAIYNLQWFRQDPGKGLTSLLLIQSSQREQTSGRLNASLDKSSGR
STLYIAASQPGDSATYLCAV<u>DSHP</u>SNYKLTFGKGTLLTVNP
(SEQ ID NO:16)

Figure 6f

KQEVTQIPAALSVPEGENLVLNCSFTDSAIYNLQWFRQDPGKGLTSLLLIQSSQREQTSGRLNASLDKSSGR
STLYIAASQPGDSATYLCAV<u>DAAQ</u>SNYKLTFGKGTLLTVNP
(SEQ ID NO:17)

Figure 6g

KQEVTQIPAALSVPEGENLVLNCSFTDSAIYNLQWFRQDPGKGLTSLLLIQSSQREQTSGRLNASLDKSSGR
STLYIAASQPGDSATYLCAVNS<u>WTGG</u>YKLTFGKGTLLTVNP
(SEQ ID NO:18)

Figure 6h

KQEVTQIPAALSVPEGENLVLNCSFTDSAIYNLQWFRQDPGKGLTSLLLIQSSQREQTSGRLNASLDKSSGR
STLYIAASQPGDSATYLCAVDWHPSNYKLTFGKGTLLTVNP
(SEQ ID NO:19)

Figure 6i

KQEVTQIPAALSVPEGENLVLNCSFTDSAIYNLQWFRQDPGKGLTSLLLIQSSQREQTSGRLNASLDKSSGR
STLYIAASQPGDSATYLCAVDSQDSNYKLTFGKGTLLTVNP
(SEQ ID NO:20)

Figure 6j

KQEVTQIPAALSVPEGENLVLNCSFTDSAIYNLQWFRQDPGKGLTSLLLIQSSQREQTSGRLNASLDKSSGR
STLYIAASQPGDSATYLCAVNSYYDGYKLTFGKGTLLTVNP
(SEQ ID NO:21)

Figure 6k

KQEVTQIPAALSVPEGENLVLNCSFTDSAIYNLQWFRQDPGKGLTSLLLIQSSQREQTSGRLNASLDKSSGR
STLYIAASQPGDSATYLCAVDTMDSNYKLTFGKGTLLTVNP
(SEQ ID NO:22)

Figure 6l

KQEVTQIPAALSVPEGENLVLNCSFTDSAIYNLQWFRQDPGKGLTSLLLIQSSQREQTSGRLNASLDKSSGR
STLYIAASQPGDSATYLCAVDHHPSNYKLTFGKGTLLTVNP
(SEQ ID NO:23)

Figure 6m

KQEVTQIPAALSVPEGENLVLNCSFTDSAIYNLQWFRQDPGKGLTSLLLIQSSQREQTSGRLNASLDKSSGR
STLYIAASQPGDSATYLCAVNSIYGDYKLTFGKGTLLTVNP
(SEQ ID NO:24)

Figure 6n

KQEVTQIPAALSVPEGENLVLNCSFTDSAIYNLQWFRQDPGKGLTSLLLIQSSQREQTSGRLNASLDKSSGR
STLYIAASQPGDSATYLCAVNSGGSNYKLTFGKGTLLTVNPNIQNPDPAVYQLRDSKSSDKSVCLFTDFDSQ
TNVSQSKDSDVYITDKCVLDMRSMDFKSNSAVAWSNKSDFACANAFNNSIIPEDTFFPSPESS
(SEQ ID NO:26)

Figure 7a

GAGVSQSPRYKVAKRGQDVALRCDPISGHVSLFWYQQALGQGPEFLTYFQNEAQLDKSGLPSDRFFAERPEG
SVSTLKIQRTQQEDSAVYLCASSLFGQGREKLFFGSGTQLSVLEDLKNVFPPEVAVFEPSEAEISHTQKATL
VCLATGFYPDHVELSWWVNGKEVHSGVCTDPQPLKEQPALNDSRYALSSRLRVSATFWQDPRNHFRCQVQFY
GLSENDEWTQDRAKPVTQIVSAEAWGRAD
(SEQ ID NO:27)

Figure 7b

KQEVTQIPAALSVPEGENLVLNCSFTDSAIYNLQWFRQDPGKGLTSLLLIQSSQREQTSGRLNASLDKSSGR
STLYIAASQPGDSATYLCAVNSGGSNYKLTFGKGTLLTVNPNIQNPDPAVYQLRDSKSSDKSVCLFTDFDSQ
TNVSQSKDSDVYITDKTVLDMRSMDFKSNSAVAWSNKSDFACANAFNNSIIPEDTFFPSPESSCDVKLVEKS
FETDTNLNFQNLSVIGFRILLLKVAGFNLLMTLRLWSS
(SEQ ID NO:28)

Figure 8a

GAGVSQSPRYKVAKRGQDVALRCDPISGHVSLFWYQQALGQGPEFLTYFQNEAQLDKSGLPSDRFFAERPEG
SVSTLKIQRTQQEDSAVYLCASSLFGQGREKLFFGSGTQLSVLEDLNKVFPPEVAVFEPSEAEISHTQKATL
VCLATGFFPDHVELSWWVNGKEVHSGVSTDPQPLKEQPALNDSRYCLSSRLRVSATFWQNPRNHFRCQVQFY
GLSENDEWTQDRAKPVTQIVSAEAWGRADCGFTSVSYQQGVLSATILYEILLGKATLYAVLVSALVLMAMVK
RKDF
(SEQ ID NO:29)

Figure 8b

HIGH-AFFINITY TCR FOR RECOGNIZING AFP ANTIGEN

CROSS-REFERENCE TO RELATED APPLICATIONS

This application represents the U.S. national stage entry of International Application No. PCT/CN2020/078271 filed Mar. 6, 2020, which claims priority to Chinese Patent Application No. 201910176833.6 filed Mar. 8, 2019, the disclosures of which are incorporated herein by reference in their entirety and for all purposes.

REFERENCE TO A SEQUENCE LISTING SUBMITTED VIA EFS WEB

The content of the ASCII text file of the sequence listing named "850766_00117_ST25.txt", which is 38,954 bytes in size, created on Jul. 24, 2025, and electronically submitted via Patent Center and is incorporated herein by reference in its entirety.

TECHNICAL FIELD

The present invention relates to the field of biotechnology, and more specifically to a T cell receptor (TCR) capable of recognizing a polypeptide derived from an AFP protein. The invention also relates to the preparation and use of said receptor.

BACKGROUND OF DISCLOSURE

There are only two types of molecules that can recognize antigens in a specific way. One is immunoglobulin or antibody; the other is a T cell receptor (TCR), which is a glycoprotein on the cell membrane surface in the form of a heterodimer of $\alpha$-chain/$\beta$ chain or $\gamma$ chain/$\delta$ chain. The composition of the TCRs profile of the immune system is generated by V(D)J recombination in thymus, followed by positive and negative selection. In the peripheral circumstance, TCRs mediate the specific recognition of the major histocompatibility complex-peptide complex (pMHC) by T cells, which are essential for immunological functioning of cells in the immune system.

TCR is the only receptor for specific antigen peptides presented on the major histocompatibility complex (MHC). This exogenous or endogenous peptide may be the only sign of abnormality in a cell. In the immune system, the binding of antigen-specific TCR and pMHC complex triggers direct physical contact between T cells and antigen presenting cells (APC), and then other molecules on the cell membrane surfaces of T cells and APC interact. This causes a series of subsequent cell signaling and other physiological responses, thus T cells with different antigen specificities exert immune effects on their target cells.

The MHC I and MHC II molecular ligands corresponding to TCRs are also proteins of the immunoglobulin superfamily but have specificity for antigen presentation. Different individuals have different MHCs, which can present different short peptides of one protein antigen to the surface of the respective APC cells. Human MHCs are usually called HLA genes or HLA complexes.

AFP, also known as a fetoprotein, is a protein expressed during embryonic development and is the main component of embryonic serum. During development, AFP has a relatively high level of expression in yolk sac and liver, but is subsequently inhibited. In hepatocellular carcinoma, the expression of AFP is activated. After being produced in the cell, AFP is degraded into small molecule polypeptides, and binds to MHC (major histocompatibility complex) molecules to form a complex, which is presented to the cell surface. FMNKFIYEI (SEQ ID NO: 25) is a short peptide derived from AFP antigen and a target for the treatment of AFP-related diseases.

Therefore, the FMNKFIYEI (SEQ ID NO: 25)-HLA A0201 complex provides a marker for TCR to target a tumor cell. TCR that can bind to FMNKFIYEI (SEQ ID NO: 25)-HLA A0201 complex has high application value for tumor treatment. For example, TCR that can target the tumor cell marker can be used to deliver cytotoxic agent or immunostimulant to target cells. Or TCR can be transformed into T cells, thus T cells expressing the TCR can destroy tumor cells, which is administered to patients for adoptive immunotherapy. For the former purpose, the ideal TCR is that having high affinity, which can reside on the targeted cells for a long time. For the latter purpose, it is preferable to use TCR with medium-affinity. Therefore, those skilled in the art devote themselves to developing TCR that targets tumor cell markers for different purposes.

SUMMARY OF DISCLOSURE

One purpose of the present disclosure is to provide a TCR with a higher affinity for FMNKFIYEI-HLA A0201 complex.

Another purpose of the present disclosure is to provide a method for preparing the above TCR and use thereof.

The first aspect of the present disclosure provides a T cell receptor (TCR), which has the activity of binding FMNKFIYEI (SEQ ID NO: 25)-HLA A0201 complex.

In another preferred embodiment, the T cell receptor (TCR) has the activity of binding FMNKFIYEI (SEQ ID NO: 25)-HLA A0201 complex, and the T cell receptor comprises a TCR$\alpha$ chain variable domain and a TCR$\beta$ chain variable domain, and the TCR$\alpha$ chain variable domain comprises 3 CDR regions, and the reference sequences of the 3 CDR regions of the TCR$\alpha$ chain variable domain are as follows:

CDR1$\alpha$: DSAIYN (SEQ ID NO: 34)
CDR2$\alpha$: IQSSQRE (SEQ ID NO: 35)
CDR3$\alpha$: AVNSGGSNYKLT (SEQ ID NO: 36), and CDR3a contains at least one of the following mutations:

| Residue before Mutation | Residue after mutation |
|---|---|
| N at position 3 of CDR3$\alpha$ | D or E |
| S at position 4 of CDR3$\alpha$ | D or G or A or W or T or H |
| G at position 5 of CDR3$\alpha$ | Q or A or V or H or W or Y or M or I |
| G at position 6 of CDR3$\alpha$ | D or R or P or Q or T or Y |
| S at position 7 of CDR3$\alpha$ | G or D |
| N at position 8 of CDR3$\alpha$ | G or D | and/or the $\beta$-chain variable domain of the TCR is an amino acid sequence having at least 90% sequence homology with the amino acid sequence of SEQ ID NO: 2.

In another preferred embodiment, the $\beta$-chain variable domain of the TCR is an amino acid sequence having at least 90%, 91%, 92%, 93%, 94%, 95%, 96%, 97%, 98%, 99% or 100% sequence homology with the amino acid sequence of SEQ ID NO: 2.

In another preferred embodiment, the mutation number of CDR3a of the TCR$\alpha$ chain variable domain is 1 to 4.

In another preferred embodiment, the affinity of the TCR for FMNKFIYEI (SEQ ID NO: 25)-HLA A0201 complex is at least 5-fold than that of the wild-type TCR.

In another preferred embodiment, the α-chain variable domain of the TCR comprises an amino acid sequence having at least 90%, 91%, 92%, 93%, 94%, 95%, 96%, 97%, 98%, or 99% sequence homology with the amino acid sequence of SEQ ID NO: 1.

In another preferred embodiment, the TCRβ chain variable domain comprises 3 CDR regions, and the amino acid sequences of the 3 CDR regions of the TCRβ chain variable domain are as follows:

CDR1B: SGHVS (SEQ ID NO: 37)
CDR2B: FQNEAQ (SEQ ID NO: 38)
CDR3B: ASSLFGQGREKLF (SEQ ID NO: 39).

In another preferred embodiment, the amino acid sequence of the TCR β-chain variable domain is SEQ ID NO: 2.

In another preferred embodiment, the TCR comprises a TCRα chain variable domain and a TCRβ chain variable domain, and the TCRα chain variable domain comprises CDR1α, CDR2a and CDR3α, wherein the amino acid sequence of CDR1a is DSAIYN (SEQ ID NO: 34), and the amino acid sequence of CDR2a is IQSSQRE (SEQ ID NO:

35); and the TCRβ chain variable domain comprises CDR1β, CDR2β and CDR3β, wherein the amino acid sequence of CDR1β is SGHVS (SEQ ID NO: 37), the amino acid sequence of CDR2β is FQNEAQ (SEQ ID NO: 38), and the amino acid sequence of CDR3β is ASSLFGQGREKLF (SEQ ID NO: 39).

In another preferred embodiment, the TCR comprises a TCRα chain variable domain and a TCRβ chain variable domain, and the TCRα chain variable domain comprises CDR1α, CDR2a and CDR3α, wherein the amino acid sequence of CDR1a is DSAIYN (SEQ ID NO: 34), and the amino acid sequence of CDR2a is IQSSQRE (SEQ ID NO: 35), and the amino acid sequence of CDR3a is: AV[3αX1][3aX2][3aX3][3aX4][3aX5][3aX6] YKLT.

In another preferred embodiment, [3aX1] is N or D or E.

In another preferred embodiment, [3aX2] is S or D or G or A or W or T or H.

In another preferred embodiment, [3aX3] is G or Q or A or V or H or W or Y or M or I. In another preferred embodiment, [3aX4] is G or D or R or P or Q or T or Y.

In another preferred embodiment, [3aX5] is S or G or D.

In another preferred embodiment, [3aX6] is N or G or D.

In another preferred embodiment, the TCR has a CDR selected from the group consisting of:

| CDR No. | CDR1α | CDR2α | CDR3α | CDR1β | CDR2β | CDR3β |
|---|---|---|---|---|---|---|
| 1 | DSAIYN (SEQ ID NO: 34) | IQSSQRE (SEQ ID NO: 35) | AVDSGGSNYKLT (SEQ ID NO: 53) | SGHVS (SEQ ID NO: 37) | FQNEAQ (SEQ ID NO: 38) | ASSLFGQGREKLF (SEQ ID NO: 39) |
| 2 | DSAIYN (SEQ ID NO: 34) | IQSSQRE (SEQ ID NO: 35) | AVEDQGSNYKLT (SEQ ID NO: 40) | SGHVS (SEQ ID NO: 37) | FQNEAQ (SEQ ID NO: 38) | ASSLFGQGREKLF (SEQ ID NO: 39) |
| 3 | DSAIYN (SEQ ID NO: 34) | IQSSQRE (SEQ ID NO: 35) | AVDGADSNYKLT (SEQ ID NO: 41) | SGHVS (SEQ ID NO: 37) | FQNEAQ (SEQ ID NO: 38) | ASSLFGQGREKLF (SEQ ID NO: 39) |
| 4 | DSAIYN (SEQ ID NO: 34) | IQSSQRE (SEQ ID NO: 35) | AVNSVRGGYKLT (SEQ ID NO: 42) | SGHVS (SEQ ID NO: 37) | FQNEAQ (SEQ ID NO: 38) | ASSLFGQGREKLF (SEQ ID NO: 39) |
| 5 | DSAIYN (SEQ ID NO: 34) | IQSSQRE (SEQ ID NO: 35) | AVEGARSNYKLT (SEQ ID NO: 43) | SGHVS (SEQ ID NO: 37) | FQNEAQ (SEQ ID NO: 38) | ASSLFGQGREKLF (SEQ ID NO: 39) |
| 6 | DSAIYN (SEQ ID NO: 34) | IQSSQRE (SEQ ID NO: 35) | AVDSHPSNYKLT (SEQ ID NO: 44) | SGHVS (SEQ ID NO: 37) | FQNEAQ (SEQ ID NO: 38) | ASSLFGQGREKLF (SEQ ID NO: 39) |
| 7 | DSAIYN (SEQ ID NO: 34) | IQSSQRE (SEQ ID NO: 35) | AVDAAQSNYKLT (SEQ ID NO: 45) | SGHVS (SEQ ID NO: 37) | FQNEAQ (SEQ ID NO: 38) | ASSLFGQGREKLF (SEQ ID NO: 39) |
| 8 | DSAIYN (SEQ ID NO: 34) | IQSSQRE (SEQ ID NO: 35) | AVNSWTGGYKLT (SEQ ID NO: 46) | SGHVS (SEQ ID NO: 37) | FQNEAQ (SEQ ID NO: 38) | ASSLFGQGREKLF (SEQ ID NO: 39) |
| 9 | DSAIYN (SEQ ID NO: 34) | IQSSQRE (SEQ ID NO: 35) | AVDWHPSNYKLT (SEQ ID NO: 47) | SGHVS (SEQ ID NO: 37) | FQNEAQ (SEQ ID NO: 38) | ASSLFGQGREKLF (SEQ ID NO: 39) |
| 10 | DSAIYN (SEQ ID NO: 34) | IQSSQRE (SEQ ID NO: 35) | AVDSQDSNYKLT (SEQ ID NO: 48) | SGHVS (SEQ ID NO: 37) | FQNEAQ (SEQ ID NO: 38) | ASSLFGQGREKLF (SEQ ID NO: 39) |
| 11 | DSAIYN (SEQ ID NO: 34) | IQSSQRE (SEQ ID NO: 35) | AVNSYYDGYKLT (SEQ ID NO: 49) | SGHVS (SEQ ID NO: 37) | FQNEAQ (SEQ ID NO: 38) | ASSLFGQGREKLF (SEQ ID NO: 39) |
| 12 | DSAIYN (SEQ ID NO: 34) | IQSSQRE (SEQ ID NO: 35) | AVDTMDSNYKLT (SEQ ID NO: 50) | SGHVS (SEQ ID NO: 37) | FQNEAQ (SEQ ID NO: 38) | ASSLFGQGREKLF (SEQ ID NO: 39) |
| 13 | DSAIYN (SEQ ID NO: 34) | IQSSQRE (SEQ ID NO: 35) | AVDHHPSNYKLT (SEQ ID NO: 51) | SGHVS (SEQ ID NO: 37) | FQNEAQ (SEQ ID NO: 38) | ASSLFGQGREKLF (SEQ ID NO: 39) |

-continued

| CDR No. | CDR1α | CDR2α | CDR3α | CDR1β | CDR2β | CDR3β |
|---------|-------|-------|-------|-------|-------|-------|
| 14 | DSAIYN (SEQ ID NO: 34) | IQSSQRE (SEQ ID NO: 35) | AVNSIYGDYKLT (SEQ ID NO: 52) | SGHVS (SEQ ID NO: 37) | FQNEAQ (SEQ ID NO: 38) | ASSLFGQGREKLF (SEQ ID NO: 39). |

In another preferred embodiment, the TCR is soluble.

In another preferred embodiment, the TCR is an αβ heterodimeric TCR, which comprises an α-chain TRAC constant region sequence and a β-chain TRBC1 or TRBC2 constant region sequence.

In another preferred embodiment, the TCR comprises (i) all or part of the TCRα chain excluding its transmembrane domain, and (ii) all or part of the TCRβ chain excluding its transmembrane domain, wherein (i) and (ii) both contain the variable domain and at least a part of the constant domain of the TCR chain.

In another preferred embodiment, the α-chain constant region and the β-chain constant region of the TCR contain an artificial inter-chain disulfide bond between them.

In another preferred embodiment, the cysteine residues forming the artificial inter-chain disulfide bond between the constant regions of the TCRα and β-chains substitutes for one or more combinations of sites selected from the group consisting of:

Thr48 in exon 1 of TRAC*01 and Ser57 in exon 1 of TRBC2*01 or TRBC1*01;

Thr45 in exon 1 of TRAC*01 and Ser77 in exon 1 of TRBC2*01 or TRBC1*01;

Tyr10 in exon 1 of TRAC*01 and Ser17 in exon 1 of TRBC2*01 or TRBC1*01;

Thr45 in exon 1 of TRAC*01 and Asp59 in exon 1 of TRBC2*01 or TRBC1*01;

Ser15 in exon 1 of TRAC*01 and Glu15 in exon 1 of TRBC2*01 or TRBC1*01;

Arg53 in exon 1 of TRAC*01 and Ser54 in exon 1 of TRBC2*01 or TRBC1*01;

Pro89 in exon 1 of TRAC*01 and Ala19 in exon 1 of TRBC2*01 or TRBC1*01; and

Tyr10 in exon 1 of TRAC*01 and Glu20 in exon 1 of TRBC2*01 or TRBC1*01.

In another preferred embodiment, the amino acid sequence of the α-chain variable domain of the TCR is selected from the group consisting of: SEQ ID NO: 11-24; and/or the amino acid sequence of the β-chain variable domain of the TCR is SEQ ID NO: 2.

In another preferred embodiment, the TCR is selected from the group consisting of:

| TCR No. | Sequence of α-chain variable domain SEQ ID NO: | Sequence of β-chain variable domain SEQ ID NO: |
|---------|------------------------------------------------|------------------------------------------------|
| 1 | 11 | 2 |
| 2 | 12 | 2 |
| 3 | 13 | 2 |
| 4 | 14 | 2 |
| 5 | 15 | 2 |
| 6 | 16 | 2 |
| 7 | 17 | 2 |
| 8 | 18 | 2 |
| 9 | 19 | 2 |
| 10 | 20 | 2 |
| 11 | 21 | 2 |
| 12 | 22 | 2 |

-continued

| TCR No. | Sequence of α-chain variable domain SEQ ID NO: | Sequence of β-chain variable domain SEQ ID NO: |
|---------|------------------------------------------------|------------------------------------------------|
| 13 | 23 | 2 |
| 14 | 24 | 2. |

In another preferred embodiment, the TCR is a single-chain TCR.

In another preferred embodiment, the TCR is a single-chain TCR consisting of an α-chain variable domain and a β-chain variable domain, and the α-chain variable domain and the β-chain variable domain are linked by a flexible short peptide sequence (linker).

In another preferred embodiment, a conjugate is bound to the C- or N-terminus of the α-chain and/or β-chain of the TCR.

In another preferred embodiment, the conjugate that binds to the TCR is a detectable label, a therapeutic agent, a PK modified portion, or a combination thereof.

In another preferred embodiment, the therapeutic agent that binds to the TCR is an anti-CD3 antibody linked to the C- or N-terminus of the α- or β-chain of the TCR.

In a preferred embodiment of the present disclosure, the affinity of the TCR for FMNKFIYEI (SEQ ID NO: 25)-HLA A0201 complex is at least 5-fold greater than that of the wild-type TCR; preferably, at least 10-fold greater; more preferably, at least 50-fold greater.

In a preferred embodiment, the affinity of the TCR for FMNKFIYEI (SEQ ID NO: 25)-HLA A0201 complex is at least 100-fold greater than that of the wild-type TCR; preferably, at least 500-fold greater; more preferably, at least 1000-fold greater.

Specifically, the dissociation equilibrium constant of the TCR to FMNKFIYEI (SEQ ID NO: 25)-HLA A0201 complex is $K_D \leq 20$ μM; preferably, $5$ μM $\leq K_D \leq 10$ μM.

In another preferred embodiment, the dissociation equilibrium constant of the TCR to FMNKFIYEI (SEQ ID NO: 25)-HLA A0201 complex is $0.1$ μM $K_D \leq 1$ μM; preferably, $1$ nM $\leq K_D \leq 100$ nM.

In a preferred embodiment of the present disclosure, the T cell receptor (TCR) has the activity of binding to FMNK-FIYEI (SEQ ID NO: 25)-HLA A0201 complex and comprises a TCRα chain variable domain and a TCRβ chain variable domain, the TCR comprises a mutation in the α-chain variable domain shown in SEQ ID NO: 1, and the mutated amino acid residue sites include one or more of 93N, 94S, 95G, 96G, 97S, and 98N, wherein the amino acid residues are designated according to the amino acid numbering of SEQ ID NO:1;

Preferably, the mutated TCRα chain variable domain includes one or more amino acid residues selected from the group consisting of: 93D or 93E; 94D or 94G or 94A or 94W or 94T or 94H; 95Q or 95A or 95V or 95H Or 95W or 95Y or 95M or 95I; 96D or 96R or 96P or 96Q or 96T or 96Y;

97G or 97D; and 98G or 98D, wherein the amino acid residues are designated according to the amino acid numbering of SEQ ID NO: 1.

The second aspect of the present disclosure provides a multivalent TCR complex comprising at least two TCR molecules, and at least one of the TCR molecules is the TCR according to the first aspect of the present disclosure.

The third aspect of the present disclosure provides a nucleic acid molecule comprising a nucleic acid sequence encoding the TCR molecule according to the first aspect of the present disclosure or the multivalent TCR complex according to the second aspect of the present disclosure, or a complementary sequence thereof.

The fourth aspect of the present disclosure provides a vector containing the nucleic acid molecule according to the third aspect of the present disclosure.

The fifth aspect of the present disclosure provides a host cell containing the vector according to the fourth aspect of the present disclosure, or having the exogenous nucleic acid molecule according to the third aspect of the present disclosure integrated into the chromosome of the cell.

The sixth aspect of the present disclosure provides an isolated cell expressing the TCR according to the first aspect of the present disclosure.

The seventh aspect of the present disclosure provides a pharmaceutical composition containing a pharmaceutically acceptable carrier and the TCR according to the first aspect of the present disclosure, or the TCR complex according to the second aspect of the present disclosure, or the cell according to the sixth aspect of the present disclosure.

The eighth aspect of the present disclosure provides a method for treating a disease, comprising administering an appropriate amount of the TCR according to the first aspect of the present disclosure, or the TCR complex according to the second aspect of the present disclosure, or the cell according to the sixth aspect of the disclosure, or the pharmaceutical composition according to the seventh aspect of the disclosure to a subject in need thereof.

Preferably, the disease is an AFP-positive tumor.

Preferably, the AFP-positive tumor is liver cancer, breast cancer or germ cell tumor; more preferably, the AFP-positive tumor is hepatocellular carcinoma.

The ninth aspect of the present disclosure provides the use of the TCR according to the first aspect of the present disclosure, or the TCR complex according to the second aspect of the present disclosure, or the cell according to the sixth aspect of the present disclosure, in the manufacture of a medicament for treating a tumor.

Preferably, the tumor is an AFP-positive tumor.

Preferably, the AFP-positive tumor is liver cancer, breast cancer or germ cell tumor; more preferably, the AFP-positive tumor is hepatocellular carcinoma.

The tenth aspect of the present disclosure provides a method for preparing the T cell receptor according to the first aspect of the present disclosure, including the steps:

(i) culturing the host cell according to the fifth aspect of the present disclosure to express the T cell receptor according to the first aspect of the present disclosure;

(ii) isolating or purifying the T cell receptor.

It should be understood that, within the scope of the present disclosure, the above technical features of the present disclosure and the technical features specifically described in the following (e.g., Examples) can be combined with each other, thereby forming new or preferred technical solution(s). Due to space limitations, they will not be elaborated herein.

BRIEF DESCRIPTION OF DRAWINGS

FIGS. 1a and 1b respectively show the amino acid sequences of wild-type TCRα and β chain variable domains that can specifically bind to FMNKFIYEI (SEQ ID NO: 25)-HLA A0201 complex.

FIGS. 2a and 2b respectively show the amino acid sequence of the α variable domain and the amino acid sequence of the β chain variable domain of the single-chain template TCR constructed in the present disclosure.

FIGS. 3a and 3b respectively show the DNA sequence of the α variable domain and the DNA sequence of the γ chain variable domain of the single-chain template TCR constructed in the present disclosure.

FIGS. 4a and 4b respectively show the amino acid sequence and nucleotide sequence of the linker of the single-stranded template TCR constructed in the present disclosure.

FIGS. 5a and 5b respectively show the amino acid sequence and DNA sequence of the single-stranded template TCR constructed in the present disclosure.

FIGS. 6a-n respectively show the amino acid sequence of the α chain variable domain of a heterodimeric TCR with high affinity for FMNKFIYEI (SEQ ID NO: 25)-HLA A0201 complex. The mutated residues are underlined.

FIGS. 7a and 7b respectively show the amino acid sequences of the reference TCR α and β chains of the present disclosure.

FIGS. 8a and 8b respectively show the amino acid sequences of wild-type TCRα and β chain that can specifically bind to FMNKFIYEI (SEQ ID NO: 25)-HLA A0201 complex.

DETAILED DESCRIPTION

Figure 9:
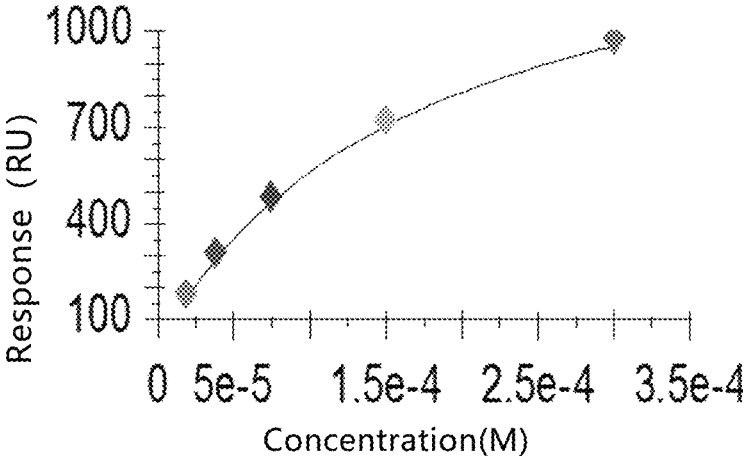
FIG. 9 is the binding curve of the reference TCR (the wild-type TCR) and FMNKFIYEI (SEQ ID NO: 25)-HLA A0201 complex.
Figure 10A:
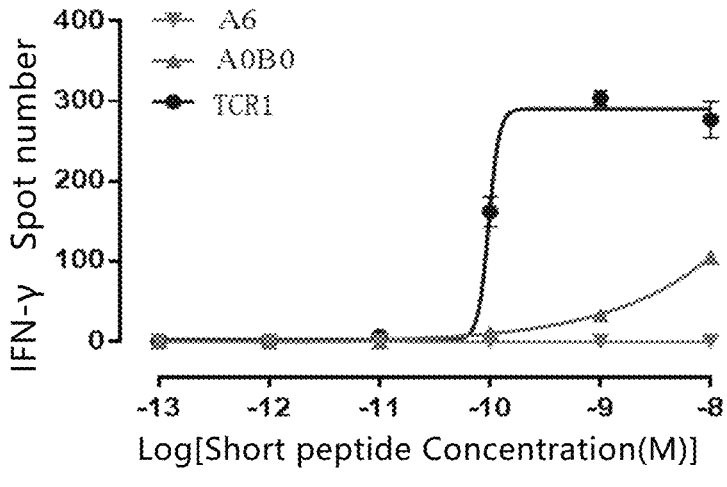
FIGS. 10a-f show the results of the activation of the effector cells transfected with the high-affinity TCR of the present disclosure against T2 cells loaded with specific short peptides.
Figure 10B:
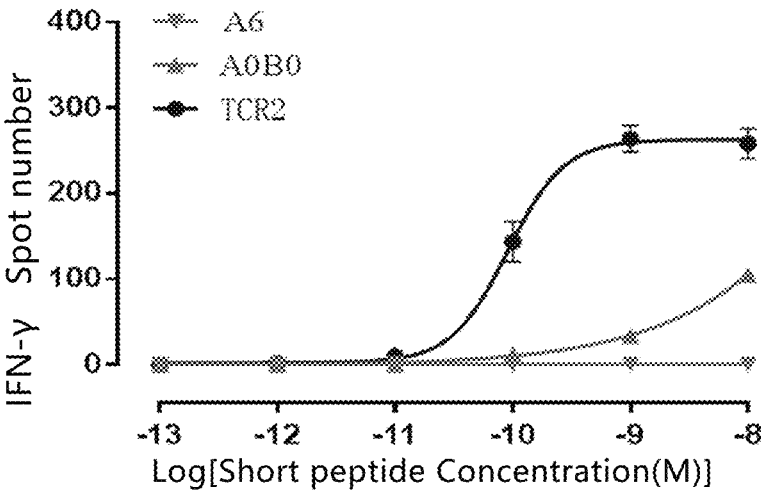
Figure 10C:
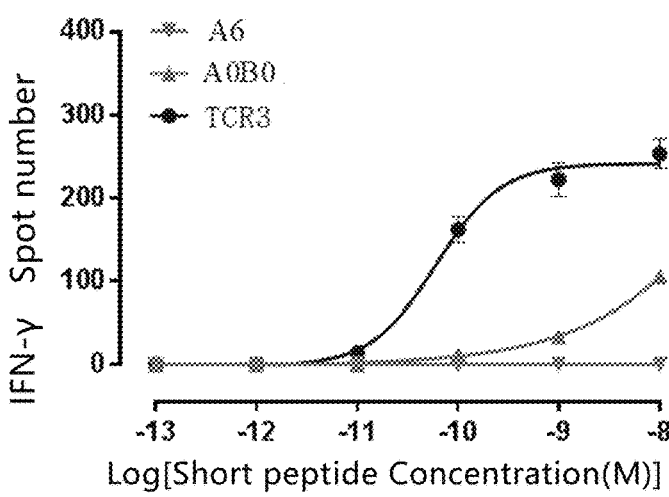
Figure 10D:
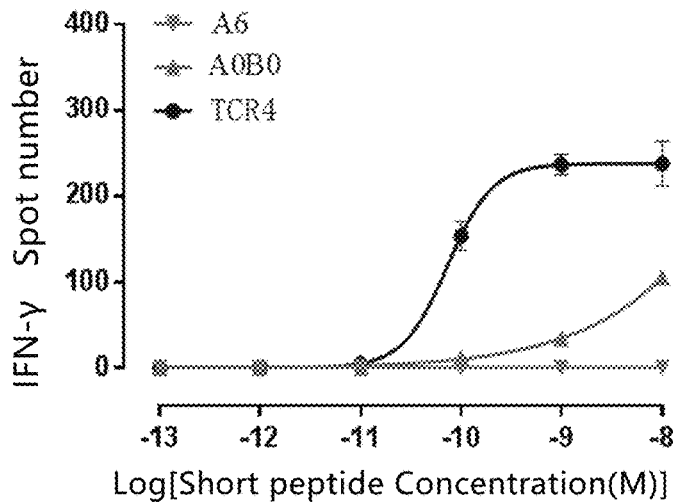
Figure 10E:
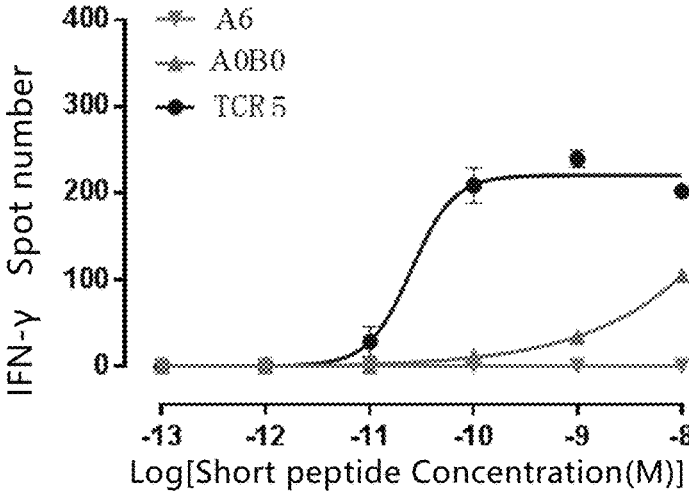
Figure 10F:
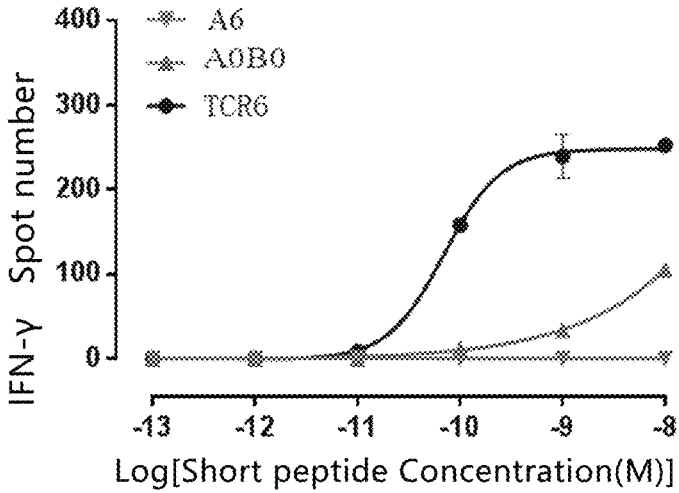

Through extensive and intensive research, a high affinity T cell receptor (TCR) that recognizes FMNKFIYEI (SEQ ID NO: 25) short peptide (derived from AFP protein) was obtained, and the FMNKFIYEI (SEQ ID NO: 25) short peptide is presented in a form of peptide-HLA A0201 complex. The high affinity TCR has a mutation in three CDR regions of its α chain variable domain:

CDR1α: DSAIYN (SEQ ID NO: 34)

CDR2α: IQSSQRE (SEQ ID NO: 35)

CDR3α: AVNSGGSNYKLT (SEQ ID NO: 36);

and after mutation, the affinity and/or binding half-life of the TCR of the present disclosure for above FMNKFIYEI (SEQ ID NO: 25)-HLA A0201 complex is at least 5-fold greater than that of the wild-type TCR.

Before the present disclosure is described, it is to be understood that the disclosure is not limited to the specific methods and experimental conditions described, as such methods and conditions may vary. It is also to be understood that the terminology used herein is for the purpose of describing particular embodiments, and is not intended to be limiting, and the scope of the present disclosure shall be only limited by the attached claim set.

All technical and scientific terms used herein have the same meaning as commonly understood by a skilled person in the art to which this disclosure belongs, unless otherwise defined.

Although any methods and materials similar or equivalent to those described in the present disclosure can be used in the practice or testing of the present disclosure, the preferred methods and materials are exemplified herein.

Terms

T Cell Receptor (TCR)

International Immunogenetics Information System (IMGT) can be used to describe a TCR. A native αβ heterodimeric TCR has an α chain and β chain. Generally speaking, each chain comprises a variable region, a junction region and a constant region, and the β chain typically also contains a short hypervariable region between the variable region and junction region, which however is often considered as a part of the junction region. The TCR junction region is determined by the unique TRAJ and TRBJ of IMGT, and the constant region of a TCR is determined by TACT and TRBC of IMGT.

Each variable region comprises three CDRs (complementarity determining regions), CDR1, CDR2 and CDR3, which are chimeric in the framework sequence. In IMGT nomenclature, the different numbers of TRAV and TRBV refer to different Va types and VB types, respectively. In IMGT system, there are following symbols for a chain constant domain: TRAC*01, wherein "TR" represents T cell receptor gene; "A" represents α chain gene; C represents the constant region; "*01" represents allele 1. There are following symbols for β-chain constant domain: TRBC1*01 or TRBC2*01, where "TR" represents T cell receptor gene; "B" represents β-chain gene; C represents constant region; "*01" represents allele 1. The constant region of a chain is uniquely defined, and in the form of β chain, there are two possible constant region genes "C1" and "C2". A skilled person in the art can obtain constant region gene sequences of TCR α and β chains through the disclosed IMGT database.

The α and β chains of TCR are generally considered as having two "domains" respectively, i.e., variable domain and constant domain. The variable domain is composed of a connected variable region and connection region. Therefore, in the specification and claims of the present application, "TCR α chain variable domain" refers to a connected TRAV and TRAJ region, and likewise, "TCR β chain variable domain" refers to a connected TRBV and TRBD/TRBJ region. The three CDRs of TCR α chain variable domain are CDR1α, CDR2a and CDR3α, respectively; and the three CDRs of TCR β chain variable domain are CDR1β, CDR2β and CDR3β, respectively. The framework sequences of TCR variable domains of the disclosure may be of murine or human origin, preferably of human origin. The constant domain of TCR comprises an intracellular portion, a transmembrane region, and an extracellular portion.

The α chain amino acid sequence and β chain amino acid sequence of the "wild type TCR" described in the present disclosure are SEQ ID NO: 28 and SEQ ID NO: 29, respectively, as shown in FIGS. 8a and 8b. In the present disclosure, the α chain amino acid sequence and β chain amino acid sequence of the "reference TCR" are SEQ ID NO: 26 and SEQ ID NO: 27, respectively, as shown in FIGS. 7a and 7b. In the present disclosure, the α and β chain variable domain amino acid sequences of the wild type TCR capable of binding to FMNKFIYEI (SEQ ID NO: 25)-HLA A0201 complex are SEQ ID NO: 1 and SEQ ID NO: 2, respectively, as shown in FIGS. 1a and 1b. In the present disclosure, the terms "polypeptide of the present disclosure", "TCR of the present disclosure" and "T cell receptor of the present disclosure" are used interchangeably.

Natural Inter-Chain Disulfide Bond and Artificial Inter-Chain Disulfide Bond

A group of disulfide bonds is present between the Ca and CB chains in the membrane proximal region of a native TCR, which is named herein as "natural inter-chain disulfide bond". In the present disclosure, an inter-chain covalent disulfide bond which is artificially introduced and the position of which is different from the position of a natural inter-chain disulfide bond is named as "artificial inter-chain disulfide bond".

For convenience of description, in the present disclosure, the positions of the amino acid sequences of TRAC*01 and TRBC1*01 or TRBC2*01 are sequentially numbered in order from N-terminal to C-terminal. For example, the 60th amino acid in the order from N-terminal to C-terminal in TRBC1*01 or TRBC2*01 is P (proline), which can be described as Pro60 of TRBC1*01 or TRBC2*01 exon 1, and can also be expressed as the amino acid at position 60 of TRBC1*01 or TRBC2*01 exon 1 in the present disclosure. For another example, the $61^{st}$ amino acid in the order from N-terminal to C-terminal in TRBC1*01 or TRBC2*01 is Q (glutamine), which can be described as Gln61 of TRBC1*01 or TRBC2*01 exon 1, and can also be expressed as the amino acid at position 61 of TRBC1*01 or TRBC2*01 exon 1 in the present disclosure, and so on. In the present disclosure, if the sequence positions of other amino acids are specifically described, the special description shall prevail.

Tumor

The term "tumor" includes all types of cancer cell growth or carcinogenic processes, metastatic tissues or malignant transformed cells, tissues or organs, regardless of pathological type or stage of infection. Examples of tumors include, without limitation, solid tumors, soft tissue tumors, and metastatic lesions. Examples of solid tumors include: malignant tumors of different organ systems, such as sarcoma, lung squamous cell carcinoma, and cancer. For example, infected prostate, lung, breast, lymph, gastrointestinal (e.g., colon) and genitourinary tract (e.g., kidney, epithelial cells), pharynx. Squamous cell carcinoma of lung includes malignant tumors, for example, most of colon cancer, rectal cancer, renal cell carcinoma, liver cancer, non-small cell cancer of lung, small intestine cancer and esophageal cancer. Metastatic lesions of the above cancers can likewise be treated and prevented using the methods and compositions of the disclosure.

DETAILED DESCRIPTION OF THE DISCLOSURE

It is well known that the α chain variable domain and the β chain variable domain of a TCR each contain three CDRs (similar to the complementarity determining regions of antibodies). CDR3 interacts with the antigen short peptide, and CDR1 and CDR2 interact with HLA. Therefore, the CDRs of a TCR molecule determine its interaction with the antigen short peptide-HLA complex. The amino acid sequences of a chain variable domain and β chain variable domain of a wild type TCR capable of binding the complex of antigen short peptide FMNKFIYEI and HLA-A0201 (i.e., FMNKFIYEI (SEQ ID NO: 25)-HLA-A0201 complex) are SEQ ID NO: 1 and SEQ ID NO: 2, respectively. These sequences were firstly discovered by the inventors. They have the following CDR regions:

α chain variable domain CDR CDR1α: DSAIYN (SEQ ID NO: 34)
CDR2α: IQSSQRE (SEQ ID NO: 35)
CDR3α: AVNSGGSNYKLT (SEQ ID NO: 36)
and β chain variable domain CDR CDR1β: SGHVS (SEQ ID NO: 37)
CDR2β: FQNEAQ (SEQ ID NO: 38)
CDR3: ASSLFGQGREKLF (SEQ ID NO: 39)

In the present disclosure, a high affinity TCR is obtained by subjecting above CDR regions to mutation and screen, which has an affinity for FMNKFIYEI (SEQ ID NO: 25)-HLA-A0201 complex that is at least 5 times greater than that of a wild type TCR for FMNKFIYEI (SEQ ID NO: 25)-HLA-A0201 complex.

In the present disclosure, a T cell receptor (TCR) is provided, which has an activity of binding to FMNKFIYEI (SEQ ID NO: 25)-HLA-A0201 complex.

The T cell receptor comprises a TCR α chain variable domain and a TCR β chain variable domain, the TCR α chain variable domain comprises three CDR regions, and the reference sequences of the three CDR regions of the TCR α chain variable domain are listed as follows, CDR1α: DSAIYN (SEQ ID NO: 34)
CDR2α: IQSSQRE (SEQ ID NO: 35)
CDR3α: AVNSGGSNYKLT (SEQ ID NO: 36), and contains at least one of the following mutations:

| CDR3α: AVNSGGSNYKLT, and contains at least one of the following mutations: | |
|---|---|
| Residue before mutation | Residue after mutation |
| N at position 3 of CDR3α | D or E |
| S at position 4 of CDR3α | D or G or A or W or T or H |
| G at position 5 of CDR3α | Q or A or V or H or W or Y or M or I |
| G at position 6 of CDR3α | D or R or P or Q or T or Y |
| S at position 7 of CDR3α | G or D |
| N at position 8 of CDR3α | G or D | and/or, the TCR β chain variable domain comprises three CDR regions, and the reference sequences of the three CDR regions of the TCR β chain variable domain are listed as follows, CDR1β: SGHVS (SEQ ID NO: 37)
CDR2β: FQNEAQ (SEQ ID NO: 38)
CDR3β: ASSLFGQGREKLF (SEQ ID NO: 39).

In particular, the number of mutations in the CDR regions of the TCR α chain may be 1, 2, 3, 4, 5, or 6.

Moreover, the TCR of the present disclosure is an αβ heterodimeric TCR, and the α chain variable domain of the TCR comprises an amino acid sequence having at least 85%, preferably at least 90%; preferably at least 92%; more preferably, at least 94% (e.g., may be at least 88%, 89%, 90%, 91%, 92%, 93%, 94%, 95%, 96%, 97%, 98%, 99% sequence homology) sequence homology with the amino acid sequence shown in SEQ ID NO: 1; and/or the γ chain variable domain of the TCR comprises an amino acid sequence having at least 90%, preferably at least 92%; more preferably, at least 94% (e.g., may be at least 91%, 92%, 93%, 94%, 95%, 96%, 97%, 98%, 99% or 100% sequence homology) sequence homology with the amino acid sequence shown in SEQ ID NO: 2.

Additionally, the TCR of the present disclosure is a single-chain TCR, and the α chain variable domain of the TCR comprises an amino acid sequence having at least 85%, preferably at least 90%; more preferably, at least 92%; most preferably at least 94% (e.g., may be at least 88%, 89%, 90%, 91%, 92%, 93%, 94%, 95%, 96%, 97%, 98%, 99% sequence homology) sequence homology with the amino acid sequence shown in SEQ ID NO: 3; and/or the γ chain variable domain of the TCR comprises an amino acid sequence having at least 85%, preferably at least 90%; more preferably, at least 92%; most preferably at least 94% (e.g., may be at least 91%, 92%, 93%, 94%, 95%, 96%, 97%, 98%, 99% sequence homology) sequence homology with the amino acid sequence shown in SEQ ID NO: 4.

In the present disclosure, the three CDRs of a chain variable domain SEQ ID NO: 1 of the wild type TCR, i.e., CDR1, CDR2 and CDR3 are located at positions 27-32, 50-56 and 91-102 of SEQ ID NO: 1, respectively. Accordingly, the amino acid residue is numbered as shown in SEQ ID NO: 1, 93N is N at the 3rd position of CDR3α, 94S is S at the 4th position of CDR3α, 95G is G at the 5th position of CDR3α, 96G is G at the 6th position of CDR3α, 97S is S at the 7th position of CDR3α, 98N is N at the 8th position of CDR3α.

The present disclosure provides a TCR having the activity of binding to FMNKFIYEI (SEQ ID NO: 25)-HLA A0201 complex and comprises a TCRα chain variable domain and a TCRβ chain variable domain, wherein the TCR comprises a mutation in the α-chain variable domain shown in SEQ ID NO: 1, and the mutated amino acid residue site includes one or more of 93N, 94S, 95G, 96G, 97S, and 98N, wherein the amino acid residues are designated according to the amino acid numbering of SEQ ID NO:1.

Preferably, the mutated TCRα chain variable domain includes one or more amino acid residues selected from the group consisting of: 93D or 93E; 94D or 94G or 94A or 94W or 94T or 94H; 95Q or 95A or 95V or 95H Or 95W or 95Y or 95M or 95I; 96D or 96R or 96P or 96Q or 96T or 96Y; 97G or 97D; and 98G or 98D, wherein the amino acid residues are designated according to the amino acid numbering of SEQ ID NO:1.

More specifically, in the α chain variable domain, specific forms of the mutation include one or more groups of N93/D/E, S94/D/G/A/W/T/H, G95/Q/A/V/H/W/Y/M/I, G96/D/R/P/Q/T/Y, S97/G/D, and N98/G/D.

Thr48 of the wild type TCR α chain constant region TRAC*01 exon 1 was mutated to cysteine, and Ser57 of the β chain constant region TRBC1*01 or TRBC2*01 exon 1 was mutated to cysteine according to the site-directed mutagenesis method well known to a skilled person in the art, so as to obtain a reference TCR, the amino acid sequences of which are shown in FIGS. 7a and 7b, respectively, and the mutated cysteine residues are indicated by bold letters. The above cysteine substitutions can form an artificial inter-chain disulfide bond between the constant regions of α and β chain of the reference TCR to form a more stable soluble TCR, so that it is easier to evaluate the binding affinity and/or binding half-life between TCR and FMNKFIYEI (SEQ ID NO: 25)-HLA-A2 complex. It is to be understood that the CDR regions of the TCR variable region determine its affinity for pMHC complex, therefore, the above cysteine substitutions in the TCR constant region won't affect the binding affinity and/or binding half-life of TCR. Therefore, in the present disclosure, the measured binding affinity between the reference TCR and FMNKFIYEI (SEQ ID NO: 25)-HLA-A0201 complex is considered to be the binding affinity between the wild-type TCR and FMNKFIYEI (SEQ ID NO: 25)-HLA-A0201 complex. Similarly, if the binding affinity between the TCR of the disclosure and FMNKFIYEI (SEQ ID NO: 25)-HLA-A0201 complex is determined to be at least 10 times the binding affinity between the reference TCR and FMNKFIYEI (SEQ ID NO: 25)-HLA-A0201 complex, the binding affinity between the TCR of the present disclosure and FMNKFIYEI (SEQ ID NO: 25)-HLA-A0201 complex is at least 10 times the binding affinity between the wild type TCR and FMNKFIYEI (SEQ ID NO: 25)-HLA-A0201 complex.

The binding affinity (in inverse proportion to the dissociation equilibrium constant $K_D$) and the binding half-life (expressed as $T_{1/2}$) can be determined by any suitable method. It should be understood that doubling of the affinity of the TCR will halve $K_D$. T12 is calculated as In2 divided by dissociation rate ($K_{off}$). Therefore, doubling of $T_{1/2}$ will halve $K_{off}$. Preferably, the binding affinity or binding half-life of a given TCR is detected for several times by using the same test protocol, for example 3 or more times, and the average of the results is taken. In a preferred embodiment, the affinity of soluble TCR is detected by the surface plasmon resonance (BIAcore) method in the Examples herein. The dissociation equilibrium constant $K_D$ of the reference TCR to FMNKFIYEI (SEQ ID NO: 25)-HLA-A2 complex is detected as 2.08E-04M, that is, 208 µM by the method, and in the present disclosure, the dissociation equilibrium constant $K_D$ of the wild type TCR to FMNKFIYEI (SEQ ID NO: 25)-HLA-A2 complex is also considered as 208 µM. Since doubling of the affinity of TCR will halve $K_D$, if the dissociation equilibrium constant Kp of the high affinity TCR to FMNKFIYEI (SEQ ID NO: 25)-HLA-A2 complex is detected as 2.08E-05M, i.e., 20.8 M, the affinity of the high affinity TCR for FMNKFIYEI (SEQ ID NO: 25)-HLA-A2 complex is 10 times that of the wild type TCR for FMNKFIYEI (SEQ ID NO: 25)-HLA-A2 complex. A skilled person is familiar with the conversion relationship between $K_D$ value units, i.e., 1 M=1000 µM, 1 µM=1000 nM, and 1 nM=1000 pM.

In a preferred embodiment of the present disclosure, the affinity of the TCR for FMNKFIYEI (SEQ ID NO: 25)-HLA A0201 complex is at least 5-fold greater than that of the wild-type TCR; preferably, at least 10-fold greater; more preferably, at least 50-fold greater.

In a preferred embodiment, the affinity of the TCR for FMNKFIYEI (SEQ ID NO: 25)-HLA A0201 complex is at least 100-fold greater than that of the wild-type TCR; preferably, at least 500-fold greater; more preferably, at least 1000-fold greater.

Specifically, the dissociation equilibrium constant of the TCR to FMNKFIYEI (SEQ ID NO: 25)-HLA A0201 complex is $K_D \leq 20$ µM.

In another preferred embodiment, the dissociation equilibrium constant of the TCR to FMNKFIYEI-HLA A0201 complex is 5 µM≤$K_D$≤10 µM; preferably, 0.1 µM≤$K_D$≤1 µM; more preferably, 1 nM≤$K_D$)≤100 nM.

Mutations can be carried out by any suitable method including, but not limited to, those based on polymerase chain reaction (PCR), restriction enzyme-based cloning or linkage-independent cloning (LIC) methods. Many standard molecular biology textbooks describe these methods in detail. More details about polymerase chain reaction (PCR) mutagenesis and restriction enzyme-based cloning can be found in Sambrook and Russell, (2001) Molecular Cloning-A Laboratory Manual (Third Edition) CSHL Publishing house. More information about LIC method can be found in Rashtchian, (1995) Curr Opin Biotechnol 6 (1): 30-6.

The method for producing the TCR of the present disclosure may be, but not limited to, screening for a TCR having high affinity for FMNKFIYEI (SEQ ID NO: 25)-HLA-A2 complex from a diverse library of phage particles displaying such TCRs, as described in a literature (Li, et al. (2005) Nature Biotech 23 (3): 349-354).

It is to be understood that genes expressing amino acid of α and β chain variable domains of a wild-type TCR or genes expressing amino acid of α and β chain variable domains of a slightly modified wild-type TCR can be used to prepare template TCRs. Changes necessary to produce the high affinity TCR of the disclosure are then introduced into the DNA encoding the variable domain of the template TCR.

The high affinity TCR of the present disclosure comprises one of a chain variable domain amino acid sequences of SEQ ID NO: 11, 12, 13, 14, 15, 16, 17, 18, 19, 20, 21, 22, 23 or 24, and/or β chain variable domain amino acid sequence of SEQ ID NO: 2. In the present disclosure, the amino acid sequences of the α chain variable domain and β chain variable domain which form the heterodimeric TCR molecule are preferably selected from the following Table 1:

TABLE 1

| TCR No. | Sequence of α chain variable domain SEQ ID NO: | Sequence of β chain variable domain SEQ ID NO: |
|---|---|---|
| 1 | 11 | 2 |
| 2 | 12 | 2 |
| 3 | 13 | 2 |
| 4 | 14 | 2 |
| 5 | 15 | 2 |
| 6 | 16 | 2 |
| 7 | 17 | 2 |
| 8 | 18 | 2 |
| 9 | 19 | 2 |
| 10 | 20 | 2 |
| 11 | 21 | 2 |
| 12 | 22 | 2 |
| 13 | 23 | 2 |
| 14 | 24 | 2 |

For the purposes of the present disclosure, the TCR of the disclosure is a moiety having at least one TCR α and/or TCR β chain variable domain. They usually comprise both of TCR α chain variable domain and TCR β chain variable domain. They may be αβ heterodimers or single-chain forms or any other stable forms. In adoptive immunotherapy, the full length chain of the αβ heterodimeric TCR (including the cytoplasmic and transmembrane domains) can be transfected. The TCR of the present disclosure can be used as a targeting agent for delivering a therapeutic agent to an antigen presenting cell or in combination with other molecules to prepare a bifunctional polypeptide to direct effector cells, when the TCR is preferably in a soluble form.

For stability, it is disclosed in the prior art that a soluble and stable TCR molecule can be obtained by introducing an artificial inter-chain disulfide bond between the α and β chain constant domains of a TCR, as described in PCT/CN2015/093806. Therefore, the TCR of the disclosure may be a TCR that an artificial interchain disulfide bond is introduced between the residues of its α and β chain constant domains. Cysteine residues form an artificial interchain disulfide bond between the α and β chain constant domains of the TCR. A cysteine residue can replace other amino acid residue at a suitable position in a native TCR to form an artificial interchain disulfide bond. For example, Thr48 of TRAC*01 exon 1 and Ser57 of TRBC1*01 or TRBC2*01 exon 1 can be replaced to form a disulfide bond. Other sites for introducing a cysteine residue to form a disulfide bond may be: Thr45 in TRAC*01 exon 1 and Ser77 in TRBC1*01 or TRBC2*01 exon 1; Tyr10 in TRAC*01 exon 1 and Ser17 in TRBC1*01 or TRBC2*01 exon 1; Thr45 in TRAC*01 exon 1 and Asp59 in TRBC1*01 or TRBC2*01 exon 1; Ser15 in TRAC*01 exon 1 and Glu15 in TRBC1*01 or TRBC2*01 exon 1; Arg53 in TRAC*01 exon 1 and Ser54 in TRBC1*01 or TRBC2*01 exon 1; Pro89 in TRAC*01 exon 1 and Ala19 in TRBC1*01 or TRBC2*01 exon 1; or Tyr10 in TRAC*01 exon 1 and Glu20 in TRBC1*01 or TRBC2*01 exon 1. That is, cysteine residues replace any group of the above-mentioned sites in a and β chain constant domains. At most 15, or at most 10, or at most 8 or fewer amino acids may be truncated at one or more C-termini of the constant domain of the TCR of the disclosure such that it does not include cysteine residues to achieve the purpose of deleting natural inter-chain disulfide bonds, or the cysteine residues forming a natural interchain disulfide bond can also be mutated to another amino acid for above purpose.

As described above, the TCR of the present disclosure may comprise an artificial interchain disulfide bond introduced between residues of its α and β chain constant domains. It should be noted that the introduced artificial disulfide bond as described above can be contained or not contained between the constant domains, and the TCR of the present disclosure may contain a TRAC constant domain sequence and a TRBC1 or TRBC2 constant domain sequence. The TRAC constant domain sequence and the TRBC1 or TRBC2 constant domain sequence of the TCR can be joined by a natural interchain disulfide bond present in the TCR.

Additionally, as for stability, it was also disclosed in a patent literature PCT/CN2016/077680 that the introduction of an artificial inter-chain disulfide bond between a chain variable region and β chain constant region of a TCR can significantly improve the stability of the TCR. Therefore, an artificial inter-chain disulfide bond may be contained between a chain variable region and β chain constant region of a high affinity TCR of the present disclosure. Specifically, cysteine residues forming an artificial inter-chain disulfide bond between a chain variable region and β chain constant region of the TCR are substituted for: an amino acid at position 46 of TRAV and amino acid at position 60 of TRBC1*01 or TRBC2*01 exon 1; an amino acid at position 47 of TRAV and amino acid at position 61 of TRBC1*01 or TRBC2*01 exon 1; amino acid at position 46 of TRAV and amino acid at position 61 of TRBC1*01 or TRBC2*01 exon 1; or an amino acid at position 47 of TRAV and amino acid at position 60 of TRBC1*01 or TRBC2*01 exon 1. Preferably, such a TCR may comprises (i) all or part of TCR α chain other than its transmembrane domain, and (ii) all or part of TCR β chain other than its transmembrane domain, wherein both of (i) and (ii) comprise the variable domain and at least a portion of constant domains of the TCR chain, and the α chain and β chain form a heterodimer. More preferably, such TCR may comprise α chain variable domain and β chain variable domain and all or part of β chain constant domain other than the transmembrane domain, which, however, does not comprise α chain constant domain, and the α chain variable domain and the β chain of the TCR form a heterodimer.

For stability, in another aspect, the TCR of the present disclosure also includes a TCR having a mutation in its hydrophobic core region, and these mutations in hydrophobic core region are preferably mutations capable of increasing the stability of the TCR of the present disclosure, as described in WO2014/206304. Such a TCR can have mutations at following positions in the variable domain hydrophobic core: (a and/or β chain) variable region amino acids at position 11, 13, 19, 21, 53, 76, 89, 91, 94, and/or a chain J gene (TRAJ) short peptide amino acid at reciprocal positions 3, 5, 7 and/or β chain J gene (TRBJ) short peptide amino acid at reciprocal positions 2, 4, 6, wherein the positions in amino acid sequence are numbered according to the position numbers listed in the International Immunogenetics Information System (IMGT). A skilled person in the art will know the above-described international immunogenetic information system and can obtain the position numbers of the amino acid residues of different TCRs in IMGT based on the database.

More specifically, in the present disclosure, a TCR in which there is a mutation in the hydrophobic core region may be a high-stability single-chain TCR composed of TCR α and β chain variable domains that linked by a flexible peptide chain. The CDR regions of TCR variable region determine its affinity for the short peptide-HLA complex, and mutations in hydrophobic core can increase the stability of the TCR, but won't affect its affinity for the short peptide-HLA complex. It should be noted that the flexible peptide chain in the present disclosure may be any peptide chain suitable for linking TCR α and β chain variable domains. The template chain constructed in Example 1 of the present disclosure for screening high-affinity TCRs is a high-stability single-chain TCR containing mutations in hydrophobic core as described above. The affinity of a TCR for FMNKFIYEI (SEQ ID NO: 25)-HLA-A0201 complex can be easily evaluated by using a TCR with higher stability.

The CDR regions of a chain variable domain and β chain variable domain of the single chain template TCR are identical to the CDR regions of the wild type TCR. That is, the three CDRs of a chain variable domain are CDR1α: DSAIYN (SEQ ID NO: 34), CDR2α: IQSSQRE (SEQ ID NO: 35), and CDR3α: AVNSGGSNYKLT (SEQ ID NO: 36) and the three CDRs of β chain variable domain are CDR1β: SGHVS (SEQ ID NO: 37), CDR2: FQNEAQ (SEQ ID NO: 38), and CDR3β: ASSLFGQGREKLF (SEQ ID NO: 39), respectively. The amino acid sequence (SEQ ID NO: 9) and nucleotide sequence (SEQ ID NO: 10) of the single-chain template TCR are shown in FIGS. 5a and 5b, respectively. Thus a single-chain TCR composed of α-chain variable domain and β-chain variable domain and having high affinity for FMNKFIYEI (SEQ ID NO: 25)-HLA-A0201 complex is screened out.

In the present disclosure, the three CDRs of a chain variable domain SEQ ID NO: 3 of the single-chain template TCR, i.e., CDR1, CDR2 and CDR3 are located at positions 27-32, 50-56 and 91-102 of SEQ ID NO: 3, respectively. Accordingly, the amino acid residues are numbered as shown in SEQ ID NO: 3, wherein 93N is N at the 3rd position of CDR3α, 94S is S at the 4th position of CDR3α, 95G is G at the 5th position of CDR3α, 96G is G at the 6th position of CDR3α, 97S is S at the 7th position of CDR3α, 98N is N at the 8th position of CDR3α.

The αβ heterodimer of the present disclosure having high affinity for FMNKFIYEI (SEQ ID NO: 25)-HLA-A0201 complex was obtained by transferring the CDR regions of α and β chain variable domains of the selected high affinity single-chain TCR to the corresponding positions of a chain variable domain (SEQ ID NO: 1) and β chain variable domain (SEQ ID NO: 2) of a wild type TCR.

The TCR of the present disclosure can be provided in a form of multivalent complex. The multivalent TCR complex of the present disclosure comprises a polymer formed by combining two, three, four or more TCRs of the present disclosure, for example, a tetrameric domain of p53 can be used to produce a tetramer. Alternatively, multiple TCRs of the disclosure can be combined with another molecule to form a complex. The TCR complexes of the disclosure can be used to track or target cells that present a particular antigen in vitro or in vivo, or produce intermediates of other multivalent TCR complexes with such uses.

The TCR of the present disclosure may be used alone or combined with a conjugate in a covalent manner or other manner, preferably in a covalent manner. The conjugate includes a detectable label (for diagnostic purposes, wherein the TCR is used to detect the presence of a cell presenting FMNKFIYEI (SEQ ID NO: 25)-HLA-A2 complex), a therapeutic agent, a PK (protein kinase) modifying moiety, or combination of any of the above described substances.

Detectable labels for diagnostic purposes include, but are not limited to, fluorescent or luminescent labels, radioactive labels, MRI (magnetic resonance imaging) or CT (electron computed tomography) contrast agents, or enzymes capable of producing detectable products.

Therapeutic agents that can be combined with or coupled to the TCRs of the disclosure include, but are not limited to: 1. Radionuclides (Koppe et al., 2005, Cancer metastasis reviews 24, 539); 2. Biotoxin (Chaudhary et al., 1989, Nature 339, 394; Epel et al., 2002, Cancer Immunology and Immunotherapy 51, 565); 3. Cytokines, such as IL-2, etc. (Gillies et al., 1992, National Academy of Sciences (PNAS) 89, 1428; Card et al., 2004, Cancer Immunology and Immunotherapy 53, 345; Halin et al., 2003, Cancer Research 63, 3202); 4. Antibody Fc fragment (Mosquera et al., 2005, The Journal Of Immunology 174, 4381); 5. Antibody scFv fragments (Zhu et al., 1995, International Journal of Cancer 62, 319); 6. Gold nanoparticles/Nanorods (Lapotko et al., 2005, Cancer letters 239, 36; Huang et al., 2006, Journal of the American Chemical Society 128, 2115); 7. Viral particles (Peng et al., 2004, Gene therapy 11, 1234); 8. Liposomes (Mamot et al., 2005, Cancer research 65, 11631); 9. Nano-magnetic particles; 10. Prodrug activating enzymes (e.g., DT-diaphorase (DTD) or biphenyl hydrolase-like protein (BPHL); 11. chemotherapeutic agent (e.g., cisplatin) or any form of nanoparticles, and the like.

An antibody to which the TCR of the present disclosure binds or a fragment thereof includes an anti-T cell or an NK-cell determining antibody, such as an anti-CD3 or anti-CD28 or anti-CD16 antibody, and the above antibody or a fragment thereof binds to a TCR, thereby better directing effector cells to target cells. In a preferred embodiment, the TCR of the disclosure binds to an anti-CD3 antibody or a functional fragment or variant thereof. Specifically, a fusion molecule of the TCR of the present disclosure and an anti-CD3 single-chain antibody comprises an amino acid sequence of a TCR α chain variable domain selected from the group consisting of SEQ ID NO: 11, 12, 13, 14, 15, 16, 17, 18, 19, 20, 21, 22, 23 and 24, and an amino acid sequence of a TCR β chain variable domain of SEQ ID NO: 2.

The disclosure also relates to a nucleic acid molecule encoding the TCR of the disclosure. The nucleic acid molecule of the disclosure may be in a form of DNA or RNA. The DNA may be coding strand or non-coding strand. For example, a nucleic acid sequence encoding the TCR of the disclosure may be the same as the nucleic acid sequence set forth in the Figures of the disclosure or a degenerate variant thereof. By way of example, "degenerate variant", as used herein, refers to a nucleic acid sequence which encodes a protein with a sequence of SEQ ID NO: 3, but is differences from the sequence of SEQ ID NO: 5.

The full length sequence of the nucleic acid molecule of the present disclosure or a fragment thereof can generally be obtained by, but not limited to, PCR amplification, recombinant methods or synthetic methods. At present, it is possible to obtain a DNA sequence encoding the TCR (or a fragment thereof, or a derivative thereof) of the present disclosure completely by chemical synthesis. Said DNA sequence can be introduced subsequently into various available DNA molecules (e.g. vectors) and cells that are already known in the art.

The disclosure also relates to vectors comprising the nucleic acid molecules of the disclosure, as well as host cells genetically engineered using the vectors or coding sequences of the disclosure. The disclosure also encompasses isolated cells, particularly T cells, which express the TCR of the disclosure. There are a number of methods suitable for T cell transfection with DNA or RNA encoding the high affinity TCR of the disclosure (e.g., Robbins et al., (2008) J. Immunol. 180:6116-6131). T cells expressing the high affinity TCR of the disclosure can be used in adoptive immunotherapy. A skilled person in the art can know many suitable methods for performing adoptive therapy (e.g., Rosenberg et al., (2008) Nat Rev Cancer 8 (4): 299-308).

The disclosure also provides a pharmaceutical composition, comprising a pharmaceutically acceptable carrier and a TCR of the disclosure, or a TCR complex of the disclosure, or cells presenting the TCR of the disclosure.

The disclosure also provides a method for treating a disease, comprising administering to a subject in need thereof an appropriate amount of a TCR of the disclosure, or a TCR complex of the disclosure, or cells presenting a TCR of the disclosure, or a pharmaceutical composition of the disclosure.

It should be understood that the amino acid names herein are identified by internationally accepted single English letters, and the corresponding three-letter abbreviated names of an amino acid are: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser(S), Thr (T), Trp (W), Tyr (Y), Val (V).

In the present disclosure, both of Pro60 or 60P represent proline at position 60. Further, regarding the expression of the specific form of mutation in the present disclosure, such as "N93D" represents that N at position 93 is substituted with D. Similarly, "N93D/E" means that N at position 93 is substituted with D or E, and so on.

In the art, substitution with amino acids of comparable or similar properties usually does not change the function of a protein. Adding one or more amino acids to the C-terminus and/or N-terminus usually does not alter the structure and function of the protein. Therefore, the TCR of the disclosure further includes a TCR, wherein up to 5, preferably up to 3, more preferably up to 2, the most preferably 1 amino acid (especially an amino acid located outside CDR regions) of the TCR of the disclosure is replaced by an amino acid with similar properties and its function is maintained.

The present disclosure also includes a TCR obtained from the TCR of the present disclosure by slight modification. Forms of modification (usually without change of the primary structure): chemical derivatization of the TCR of the disclosure, such as acetylation or carboxylation. Modifications also include glycosylation, such as those TCRs produced by glycosylation modifications in the synthesis and processing or in further processing steps of the TCR of the disclosure. Such modification can be accomplished by exposing the TCR to an enzyme performing glycosylation (such as mammalian glycosylase or deglycosylase). Modification forms also include sequences having phosphorylated amino acid residues (such as phosphotyrosine, phosphoserine, phosphothreonine). Also included are TCRs that have been modified to enhance their antiproteolytic properties or optimize solubility properties.

The TCR, TCR complexes of the disclosure or T cells transfected by the TCRs of the disclosure can be provided in a pharmaceutical composition together with a pharmaceutically acceptable carrier. The TCR, multivalent TCR complex or cell of the disclosure is typically provided as part of a sterile pharmaceutical composition, which typically comprises a pharmaceutically acceptable carrier. The pharmaceutical composition can be of any suitable form (depending on the desired method for administration to a patient). It can be provided in a unit dosage form, usually in a sealed container, and can be provided as part of a kit. Such kit includes (but not necessary) instructions. It can include a plurality of said unit dosage form.

Furthermore, the TCR of the disclosure may be used alone or in combination with other therapeutic agents (e.g., formulated in the same pharmaceutical composition).

The pharmaceutical composition may also contain a pharmaceutically acceptable carrier. The term "pharmaceutically acceptable carrier" refers to a carrier for the administration of a therapeutic agent. The term refers to such pharmaceutical carriers which themselves do not induce the production of antibodies harmful to the individual receiving the composition and which are not excessively toxic after administration. Such carriers are well known to those of ordinary skill in the art. A full discussion of pharmaceutically acceptable excipients can be found in Remington's Pharmaceutical Sciences (Mack Pub. Co., N. J. 1991). Such carriers include, but are not limited to, saline, buffer, dextrose, water, glycerol, ethanol, adjuvants, and combinations thereof.

The pharmaceutically acceptable carrier in the therapeutic composition may contain a liquid such as water, saline, glycerol and ethanol. In addition, auxiliary substances such as wetting or emulsifying agents, pH buffering substances and the like may also be present in these carriers.

In general, the therapeutic compositions can be formulated as injectables, such as liquid solutions or suspensions; and as solid forms which may be suitable for being formulated in solution or suspension, liquid carriers prior to injection.

Once a composition of the disclosure is formulated, it can be administered by conventional routes including, but not limited to, intraocular, intramuscular, intravenous, subcutaneous, intradermal, or topical administration, preferably parenteral, including subcutaneous, intramuscular or intravenous administration. A subject to be prevented or treated may be an animal; especially a human.

When the pharmaceutical composition of the present disclosure is used for actual treatment, pharmaceutical compositions of various dosage forms may be employed depending on the uses, preferably, an injection, an oral preparation, or the like.

These pharmaceutical compositions can be formulated by mixing, diluting or dissolving according to conventional methods, occasionally, suitable pharmaceutical additives can be added such as excipients, disintegrating agents, binders, lubricants, diluents, buffers, isotonicities, preservatives, wetting agents, emulsifiers, dispersing agents, stabilizers and co-solvents, and the formulation process can be carried out in a customary manner depending on the dosage form.

The pharmaceutical composition of the present disclosure can also be administered in the form of a sustained release dosage form. For example, the TCR of the present disclosure can be incorporated into a pill or microcapsule in which the sustained release polymer is used as a carrier, and then the pill or microcapsule is surgically implanted into the tissue to be treated. Examples of the sustained-release polymer include ethylene-vinyl acetate copolymer, polyhydrometaacrylate, polyacrylamide, polyvinylpyrrolidone, methylcellulose, lactic acid polymer, lactic acid-glycolic acid copolymer or the like, preferably biodegradable polymer, such as lactic acid polymer and lactic acid-glycolic acid copolymer.

When the pharmaceutical composition of the present disclosure is used for actual treatment, the amount of the TCR or TCR complex of the present disclosure or the cell presenting the TCR of the present disclosure as an active ingredient may be reasonably determined based on the body weight, age, sex, and degree of symptoms of each patient to be treated, and ultimately by a doctor.

Main Advantages of the Disclosure:

(1) The affinity and/or binding half-life of the TCR of the present disclosure for FMNKFIYEI-HLA-A2 complex is at least 5 times, preferably at least 10 times that of a wild type TCR.

(2) The affinity and/or binding half-life of the TCR of the present disclosure for FMNKFIYEI-HLA-A2 complex is at least 100 times, preferably at least 1000 times that of a wild type TCR.

(3) Effector cells transduced with the high-affinity TCR of the present disclosure exhibit a strong killing effect on target cells.

The disclosure is further illustrated by the specific examples described below. It should be understood that these examples are merely illustrative, and do not limit the scope of the present disclosure. The experimental methods without specifying the specific conditions in the following examples generally used the conventional conditions, such as those described in Sambrook & Russell, Molecular Cloning: A Laboratory Manual (3rd ed.) (2001) CSHL Publishing company, or followed the manufacturer's recommendation. Percentages and parts are by weight unless otherwise stated.

Materials and Methods

The experimental materials used in the examples of the present disclosure can commercially available, unless otherwise specified, wherein *E. coli* DH5a was purchased from Tiangen, *E. coli* BL21 (DE3) was purchased from Tiangen, *E. coli* Tuner (DE3) was purchased from Novagen, and plasmid pET28a was purchased from Novagen.

Example 1. Generation of Stable Single-Chain TCR Template Chains with a Mutation in Hydrophobic Core In the present disclosure, a method of site-directed mutagenesis was used according to a patent literature WO2014/206304 to construct a stable single-chain TCR molecule composed of TCR α and β-chain variable domains connected by a flexible short peptide (linker), and the amino acid and DNA sequences of which were SEQ ID NO: 9 and SEQ ID NO: 10, respectively, as shown in FIGS. 5a and 5b. The single-chain TCR molecule was used as a template for screening high-affinity TCR molecules. The amino acid sequences of a variable domain (SEQ ID NO: 3) and β variable domain (SEQ ID NO: 4) of the template chain were shown in FIGS. 2a and 2b; the corresponding DNA sequences were SEQ ID NOs: 5 and 6, respectively, as shown in FIGS. 3a and 3b; and the amino acid sequence and DNA sequence of the flexible short peptide (linker) were SEQ ID NOs: 7 and 8, respectively, as shown in FIGS. 4a and 4b.

The target gene carrying the template chain was digested with NcoI and NotI, and ligated with pET28a vector digested with NcoI and NotI. The ligation product was transformed into E. coli DH5α, plated on a kanamycin-containing LB plate, inverted and cultured at 37° C. over-night, and the positive clones were picked for PCR screen-ing. Positive recombinants were sequenced, the recombinant plasmid was extracted and transferred into E. coli BL21 (DE3) for expression after the sequence was determined to be correct.

Example 2. Expression, Re-Folding and Purification of the Stable Single-Chain TCR Constructed in Example 1

All of BL21 (DE 3) colonies containing the recombinant plasmid pET28α-template chain prepared in Example 1 were inoculated into LB medium containing kanamycin, and cultured at 37° C. until OD600 was 0.6-0.8. IPTG was added to a final concentration of 0.5 mM, and cultured at 37° C. for another 4 hrs. The cell pellets were harvested by centrifu-gation at 5000 rpm for 15 min, and the cell pellets were lysed with Bugbuster Master Mix (Merck). The inclusion bodies were recovered by centrifugation at 6000 rpm for 15 min, followed by washing with Bugbuster (Merck) to remove cell debris and membrane fraction. The inclusion bodies were collected by centrifugation at 6000 rpm for 15 min, and dissolved in a buffer (20 mM Tris-HCl pH 8.0, 8 M urea), and the insoluble matters were removed by high-speed centrifugation. The supernatant was quantitativly deter-mined by BCA method, and then dispensed and stored at −80° C. until use.

To 5 mg of dissolved single-chain TCR inclusion body protein, 2.5 mL of buffer (6 M Gua-HCl, 50 mM Tris-HCl pH 8.1, 100 mM NaCl, 10 mM EDTA) was added, then DTT was added to a final concentration of 10 mM, and incubated at 37° C. for 30 min. The single-chain TCRs as treated above was added dropwise to a 125 mL of refolding buffer (100 mM Tris-HCl pH 8.1, 0.4 M L-arginine, 5 M urea, 2 mM EDTA, 6.5 mM β-mercapthoethylamine, 1.87 mM Cysta-mine) with a syringe, and stirred at 4° C. for 10 min. Then the refolded solution was loaded into a cellulose membrane dialysis bag with a cut-off of 4 kDa, and the dialysis bag was placed in 1 L of pre-cooled water, and stirred slowly at 4° C. overnight. After 17 hours, the dialysis liquid was changed to 1 L of pre-chilled buffer (20 mM Tris-HCl pH 8.0) and dialysis was continued for 8 h at 4° C. The dialysis liquid was then replaced with the same fresh buffer and dialysis was continued overnight. After 17 hours, the sample was filtered through a 0.45 μm filter, vacuum degassed and the protein was purified through an anion exchange column (HiTrap Q HP, GE Healthcare) with a linear gradient elution of 0-1 M NaCl prepared with 20 mM Tris-HCl pH 8.0. The collected eluted fractions were subjected to SDS-PAGE analysis, and the fractions containing single-chain TCRs were concentrated and further purified by a gel filtration column (Superdex 75 10/300, GE Healthcare), and the target components were also subjected to SDS-PAGE analysis.

The eluted fractions for BIAcore analysis was further tested for purity using gel filtration. The conditions were as follows: chromatographic column of Agilent Bio SEC-3 (300 A, ¢ 7.8×300 mm), mobile phase of 150 mM phosphate buffer, flow rate of 0.5 mL/min, column temperature of 25° C., and UV detection wavelength of 214 nm.

Example 3. Binding Characterization

BIAcore Analysis

The binding activity of the TCR molecule to FMNKFI-YEI (SEQ ID NO: 25)-HLA-A0201 complex was detected using BIAcore T200 real-time analysis system. The anti-streptavidin antibody (GenScript) was added to a coupling buffer (10 mM sodium acetate buffer, pH 4.77), and then the antibody was passed through a CM5 chip pre-activated with EDC and NHS to immobilize the antibody on the surface of the chip. The unreacted activated surface was finally blocked with a solution of ethanolamine in hydrochloric acid to complete the coupling process at a coupling level of about 15,000 RU.

A low concentration of streptavidin flowed over the surface of the antibody-coated chip, then FMNKFIYEI (SEQ ID NO: 25)-HLA-A0201 complex flowed through the detection channel with another channel being used as a reference channel. 0.05 mM biotin then flowed over the chip for 2 min at a flow rate of 10 μL/min, thereby blocking the remaining binding sites for streptavidin. The affinity was determined by single-cycle kinetic analysis. TCR was diluted to several different concentrations with HEPES-EP buffer (10 mM HEPES, 150 mMNaCl, 3 mM EDTA, 0.005% P20, pH 7.4), and flowed over the surface of the chip in turn at a flow rate of 30 μL/min, with a binding time of 120 s per injection. After the last injection, the chip was left for dissociation for 600 s. At the end of each round of assay, the chip was regenerated with 10 mM Gly-HCl, pH 1.75. Kinetic parameters were calculated using BIAcore Evalua-tion software.

The preparation process for the above FMNKFIYEI (SEQ ID NO: 25)-HLA-A0201 complex was described as follows:
a. Purification 100 ml of E. coli liquid induced to express heavy or light chain was collected, and centrifuged at 8000 g for 10 min at 4° C., and the cells were washed once with 10 ml of PBS, and then vigorously shaken in 5 ml of BugBuster Master Mix Extraction Reagents (Merck) for resuspending the cells. The suspension was subjected to rotary incubation for 20 min at room temperature, and then centrifuged at 6000 g for 15 min at 4° C. The supernatant was discarded to collect inclusion bodies.

The above inclusion bodies was re-suspended in 5 ml BugBuster Master Mix and subjected to rotary incubation at room temperature for 5 min. 30 ml of 10 time-diluted BugBuster was added, mixed, and centrifuged at 6000 g for 15 min at 4° C. The supernatant was discarded, 30 ml of 10 time-diluted BugBuster was added to re-suspend the inclu-sion body, mixed, and centrifuged twice at 6000 g at 4° C. for 15 min. 30 ml of 20 mM Tris-HCl pH 8.0 was added to re-suspend the inclusion bodies, mixed, and centrifuged at 6000 g at 4° C. for 15 min. Finally, inclusion bodies were dissolved in 20 mM Tris-HCl 8M urea, and the purity of inclusion bodies was determined by SDS-PAGE and the concentration was measured by BCA kit.
b. Refolding Synthesized short peptide FMNKFIYEI (SEQ ID NO: 25) (Beijing Saibaisheng Gene Technology Co., Ltd.) were dissolved in DMSO to a concentration of 20 mg/ml. Inclu-sion bodies of light and heavy chains were solubilized in 8 M urea, 20 mM Tris pH 8.0, 10 mM DTT, and further denatured by adding 3 M guanidine hydrochloride, 10 mM sodium acetate, 10 mM EDTA before refolding. FMNKFI- YEI (SEQ ID NO: 25) peptide was added to a refolding buffer (0.4 M L-arginine, 100 mM Tris pH 8.3, 2 mM EDTA, 0.5 mM oxidized glutathione, 5 mM reduced glutathione, 0.2 mM PMSF, cooled to 4° C.) at 25 mg/L (final concentration). Then 20 mg/L of light chain and 90 mg/L of heavy chain (final concentration, heavy chain was added in three portions, 8 h/portion) were successively added, and refolded at 4° C. for at least 3 days until completion of refolding, and SDS-PAGE was used to confirm the refolding.

c. Purification Upon Refolding

The refolding buffer was replaced with 10 volumes of 20 mM Tris pH 8.0 for dialysis, and the buffer was exchanged for at least two times to substantially reduce the ionic strength of the solution. After dialysis, the protein solution was filtered through a 0.45 um cellulose acetate filter and loaded onto a HiTrap Q HP (GE, General Electric Company) anion exchange column (5 ml bed volume). The protein was eluted with a linear gradient of 0-400 mM NaCl prepared in 20 mM Tris pH 8.0 using Akta Purifier (GE), and the pMHC was eluted at approximately 250 mM NaCl. Peak fractions were collected and the purity thereof was detected by SDS-PAGE.

d. Biotinylation

Purified pMHC molecules were concentrated in a Millipore ultrafiltration tube, while the buffer was replaced with 20 mM Tris pH 8.0, and then biotinylation reagent 0.05 M Bicine pH 8.3, 10 mM ATP, 10 mM MgOAc, 50 μM D-Biotin, 100 μg/ml BirA enzyme (GST-BirA) was added. The resulting mixture was incubated at room temperature overnight, and SDS-PAGE was used to detect the completion of biotinylation.

e. Purification of Biotinylated Complex

The biotinylated and labeled pMHC molecules were concentrated to 1 ml in a Millipore ultrafiltration tube. The biotinylated pMHC was purified by gel filtration chromatography. 1 ml of concentrated biotinylated pMHC molecules was loaded on a HiPrepTM 16/60 S200 HR column (GE) pre-equilibrated with filtered PBS using an Akta Purifier (GE) and eluted with PBS at a flow rate of 1 ml/min. The biotinylated pMHC molecules were eluted as a single peak at about 55 ml. The protein-containing fractions were combined and concentrated in a Millipore ultrafiltration tube. The concentration of protein was determined by BCA method (Thermo), protease inhibitor cocktail (Roche) was added and the biotinylated pMHC molecules were dispensed and stored at −80° C.

Example 4. Generation of High-Affinity Single-Chain TCR

Phage display technology is a means to generate a high affinity TCR variant library for screening high affinity variants. The TCR phage display and screening method described by Li et al. ((2005) *Nature Biotech* 23 (3): 349-354) was applied to the single-chain TCR template of Example 1. A library of high affinity TCRs was established by mutating CDR regions of the template chain and panned. After several rounds of panning, the phage library can specifically bind to the corresponding antigen, the monoclones were picked and sequence analysis was performed.

BIAcore method of Example 3 was used to analyze the interaction between a TCR molecule and FMNKFIYEI (SEQ ID NO: 25)-HLA-A0201 complex, and a high affinity TCR with affinity and/or binding half-life of at least 5 times that of the wild-type TCR was screened out, that is, the dissociation equilibrium constant $K_D$ of the screened high affinity TCR for binding FMNKFIYEI (SEQ ID NO: 25)-

HLA-A0201 complex is less than or equal to one-fifth of the dissociation equilibrium constant $K_D$ of the wild type TCR for binding FMNKFIYEI (SEQ ID NO: 25)-HLA-A0201 complex, and the results were shown in Table 3 below. $K_D$ value of the interaction between the soluble reference TCR and FMNKFIYEI (SEQ ID NO: 25)-HLA-A0201 complex was detected to be 208 μM by using the above method, and the interaction curve is shown in FIG. 9, that is, $K_D$ value of the wild type TCR interacting with FMNKFIYEI (SEQ ID NO: 25)-HLA-A0201 complex is also 208 μM (2.08E-04M).

Upon detection, a single-chain TCR was selected with affinity for the FMNKFIYEI (SEQ ID NO: 25)-HLA-A0201 complex of at least 5 times that of the wild-type TCR for FMNKFIYEI (SEQ ID NO: 25)-HLA-A0201 complex.

Example 5. Generation of High-Affinity αβ Heterodimeric TCR

The mutations in CDR regions of the high-affinity single-chain TCRs screened in Example 4 were introduced into the corresponding sites of the variable domain of the αβ heterodimeric TCR, and its affinity for FMNKFIYEI (SEQ ID NO: 25)-HLA-A0201 complex was detected by BIAcore. The mutated sites of high-affinity can be introduced in the above CDR regions by a method of site-directed mutagenesis well known to a skilled person in the art. The amino acid sequences of a chain and β chain variable domain of the above wild type TCR were shown in FIGS. 1*a* (SEQ ID NO: 1) and 1b (SEQ ID NO: 2), respectively.

It should be noted that in order to obtain a more stable soluble TCR for easier evaluation of the binding affinity and/or binding half-life between the TCR and FMNKFIYEI (SEQ ID NO: 25)-HLA A0201 complex, the αβ heterodimeric TCR may be such a TCR in which a cysteine residue was respectively introduced into α and β chain constant domains to form an artificial inter-chain disulfide bond. In this example, the amino acid sequences of TCR α and β chains after introducing a cysteine residue were shown in FIG. 7*a* (SEQ ID NO: 26) and 7b (SEQ ID NO: 27), and the introduced cysteine residues were indicated by bold letters.

According to standard methods described in "Molecular Cloning a Laboratory Manual" (3rd edition, Sambrook and Russell), genes of extracellular sequences of the TCR α and β chains to be expressed were synthesized and inserted into an expression vector pET28α+ (Novagene), wherein the upstream and downstream cloning sites were NcoI and NotI, respectively. Mutations in the CDR regions were introduced by overlap PCR well known to a skilled person in the art. The inserted fragment was sequenced to confirm that it was correct.

Example 6. Expression, Refolding and Purification of αβ Heterodimeric TCR

Expression vectors for TCR α and β chains were transformed into the expression bacteria BL21 (DE3) by chemical transformation, respectively. The bacteria were grown in LB medium and induced with a final concentration of 0.5 mM IPTG at OD600=0.6. The inclusion bodies formed after the TCR α and β chains were expressed were extracted by BugBuster Mix (Novagene) and repeatedly washed with BugBuster solution. The inclusion bodies were finally dissolved in 6 M guanidine hydrochloride, 10 mM dithiothreitol (DTT), 10 mM ethylenediaminetetraacetic acid (EDTA) and 20 mM Tris (pH 8.1).

The dissolved TCR α and β chains were rapidly mixed in 5 M urea, 0.4 M arginine, 20 mM Tris (pH 8.1), 3.7 mM cystamine, and 6.6 mM β-mercapoethylamine (4° C.) at a mass ratio of 1:1. The final concentration was 60 mg/mL. After mixing, the solution was dialyzed against 10 volumes of deionized water (4° C.), and after 12 hours, deionized water was exchanged with a buffer (20 mM Tris, pH 8.0) and dialysis was continued at 4° C. for 12 hours. After completion of the dialysis, the solution was filtered through a 0.45 μM filter and purified through an anion exchange column (HiTrap Q HP, 5 ml, GE Healthcare). The elution peak of TCR containing successfully refolded α and β dimers was confirmed by SDS-PAGE gel. The TCR was then further purified by gel filtration chromatography (HiPrep 16/60, Sephacryl S-100 HR, GE Healthcare). The purity of the purified TCR was determined by SDS-PAGE to be greater than 90%, and the concentration thereof was determined by BCA method.

Example 7. Results of BIAcore Analysis

The affinity of the αβ heterodimeric TCR, in which a high affinity CDR region was introduced, for FMNKFIYEI (SEQ ID NO: 25)-HLA-A0201 complex was detected by using the method described in Example 3.

The CDR regions selected from the high-affinity single-chain TCR α and β chain were transferred into the corresponding positions of the wild-type TCR α chain variable domain SEQ ID NO: 1 and β chain variable domain SEQ ID NO: 2, respectively, to form an αβ heterodimeric TCR. The amino acid sequences of resulting new TCR α variable domains were shown in FIGS. 6a-n. Since the CDR regions of a TCR molecule determine their affinity for the corresponding pMHC complex, a skilled person in the art can anticipate that an αβ heterodimeric TCR, in which a high affinity mutation site was introduced also has a high affinity for FMNKFIYEI (SEQ ID NO: 25)-HLA-A0201 complex. The expression vector was constructed by the method described in Example 5, the above-mentioned αβ heterodimeric TCR with a high-affinity mutation being introduced was expressed, refolded and purified by the method described in Example 6, and then the affinity of the TCR for FMNKFIYEI (SEQ ID NO: 25)-HLA-A0201 complex was determined by BIAcore T200, as shown in Table 2 below.

TABLE 2

| TCR No. | TCR variable domain(SEQ ID NO) | | $K_D(M)$ |
|---|---|---|---|
| | α | β | |
| 1 | 11 | 2 | 5.482E−06 |
| 2 | 12 | 2 | 2.073E−06 |
| 3 | 13 | 2 | 1.377E−07 |
| 4 | 14 | 2 | 1.967E−05 |
| 5 | 15 | 2 | 7.453E−07 |
| 6 | 16 | 2 | 9.664E−08 |
| 7 | 17 | 2 | 1.620E−05 |
| 8 | 18 | 2 | 1.472E−05 |
| 9 | 19 | 2 | 9.672E−08 |
| 10 | 20 | 2 | 3.553E−07 |
| 11 | 21 | 2 | 2.091E−05 |
| 12 | 22 | 2 | 4.628E−08 |
| 13 | 23 | 2 | 2.943E−07 |
| 14 | 24 | 2 | 4.065E−07 |

As can be seen from Table 2 above, the αβ heterodimeric TCRs with mutation sites introduced into CDR regions maintained high affinity for FMNKFIYEI (SEQ ID NO: 25)-HLA-A0201 complex. The affinity of the heterodimeric TCRs for FMNKFIYEI (SEQ ID NO: 25)-HLA-A0201 complex was at least 5 times of that of the wild-type TCR.

Example 8. Expression, Refolding and Purification of Fusions of Anti-CD3 Antibodies with High-Affinity αβ Heterodimeric TCR The αβ heterodimeric TCR was fused with a single-chain molecule (scFv) of an anti-CD3 antibody to construct a fusion molecule. The anti-CD3 scFv was fused with B chain of the TCR, and the TCR β chain might comprise β chain variable domain of any of the above high-affinity αβ heterodimeric TCRs, and the TCR α chain of the fusion molecule might comprise α chain variable domain of any of the above high-affinity αβ heterodimeric TCRs.

Construction of Expression Vector for Fusion Molecule

1. Construction of Expression Vector for a Chain

The target gene carrying a chain of the αβ heterodimeric TCR was digested with NcoI and NotI, and ligated with pET28a vector digested with NcoI and NotI. The ligation product was transformed into E. coli DH5α, plated on a kanamycin-containing LB plate, inverted and cultured at 37° C. overnight, and the positive clones were picked for PCR screening. Positive recombinants were sequenced to determine the correct sequence and the recombinant plasmid was extracted and transferred into E. coli Tuner (DE3) for expression.

2. Construction of Expression Vector for Anti-CD3 (scFv)-β Chain

Primers were designed by overlapping PCR to connect genes of the anti-CD3 scFv and high-affinity heterodimeric TCRβ chain. The intermediate linker was GGGGS (SEQ ID NO:30), and the gene fragment of the fusion protein of anti-CD3 scFv and the high-affinity heterodimeric TCRβ chain had the restriction endonuclease sites NcoI (CCATGG (SEQ ID NO:31)) and NotI (GCGGCCGC (SEQ ID NO:32)). The PCR amplification product was digested with NcoI and NotI and ligated with pET28a vector digested with NcoI and NotI. The ligation product was transformed into E. coli DH5α competent cells, plated on a kanamycin-containing LB plate, and inverted and cultured overnight at 37° C. Positive clones were picked for PCR screening, and the positive recombinants were sequenced to determine the correct sequence. After confirmation the recombinant plasmids were extracted and transformed into E. coli Tuner (DE3) competent cells for expression.

Expression, Refolding and Purification of Fusion Protein

The expression plasmids were separately transformed into E. coli Tuner (DE3) competent cells, plated on LB plates (kanamycin 50 μg/mL) and cultured overnight at 37° C. On the next day, clones were picked and inoculated into 10 mL LB liquid medium (kanamycin 50 μg/mL) for 2-3 h, and inoculated into 1 L LB medium at a volume ratio of 1:100, the culture was continued until the OD600 was 0.5-0.8, and a final concentration of 1 mM IPTG was added to induce expression of the protein of interest. After induction for 4 hours, cells were harvested by centrifugation at 6000 rpm for 10 mins. The cells were washed once in PBS buffer and were dispensed, and cells corresponding to 200 mL of the bacterial culture were taken and lysed with 5 mL of BugBuster Master Mix (Merck), inclusion bodies were collected by centrifugation at 6000 g for 15 min and then washed with detergent for 4 times to remove cell debris and membrane components. The inclusion bodies were then washed with a buffer such as PBS to remove detergent and salt. Finally, the inclusion bodies were dissolved in 6M guanidine hydrochloride, 10 mM dithiothreitol (DTT), 10 mM ethylenediaminetetraacetic acid (EDTA), 20 mM Tris, pH 8.1 buffer solution, and the concentration of inclusion bodies was determined. The inclusion bodies were dispensed and cryopreserved at −80° C.

The dissolved TCRα chain and anti-CD3 (scFv)-β chain were rapidly mixed in a mass ratio of 2:5 in 5 M urea, 0.4 M L-arginine, 20 mM Tris pH 8.1, 3.7 mM cystamine, and 6.6 mM β-mercapoethylamine (4° C.), and the final concentrations of a chain and anti-CD3 (scFv)-β chain were 0.1 mg/mL, 0.25 mg/mL, respectively.

After mixing, the solution was dialyzed against 10 volumes of deionized water (4° C.), and after 12 hours, deionized water was exchanged with a buffer (10 mM Tris, pH 8.0) and dialysis was continued at 4° C. for 12 hours. After completion of the dialysis, the solution was filtered through a 0.45 μM filter and purified through an anion exchange column (HiTrap Q HP, 5 ml, GE Healthcare). The elution peak of TCR containing successfully refolded TCRα and anti-CD3 (scFv)-β chain dimers was confirmed by SDS-PAGE gel. The TCR fusion molecule was then purified by size exclusion chromatography (S-100 16/60, GE healthcare) and further purified by an anion exchange column (HiTrap Q HP 5 ml, GE healthcare). The purity of the purified TCR fusion was determined by SDS-PAGE to be greater than 90%, and the concentration thereof was determined by BCA method.

Example 9. Activation Experiment of the Effector Cells Transfected with the High-Affinity TCR of the Present Disclosure Against T2 Cells Loaded with Specific Short Peptides ELISPOT Protocol The following experiments were performed to prove the specific activation response of T cells transduced by TCR of the present disclosure to target cells. The production of IFN-γ detected by ELISPOT assay was used as the readout value of T cell activation.

Reagents
Assay medium: 10% FBS (Gibco, Cat No. 16000-044), RPMI 1640 (Gibco, Cat No. C11875500bt)
Washing buffer (PBST): 0.01M PBS/0.05% Tween 20 PBS (Gibco, Cat No. C10010500BT)
PVDF ELISPOT 96 well-plate (Merck Millipore., Cat No., MSIPS4510)
Human IFN-γ ELISPOT PVDF-Enzyme Kit (BD) contains all the other necessary reagents (capture and detection antibodies, streptavidin-alkaline phosphatase and BCIP/NBT solution)

Method
Target Cells
The target cells used in this experiment were T2 cells loaded with specific short peptides of FMNKFIYEI (SEQ ID NO: 25). The target cells were prepared in the assay medium: the concentration of target cells was adjusted to 1.0×10⁵cells/ml, and 100 microliters was added into each well to obtain 1.0×10⁴ cells/well.

Effector Cells
The effector cells (T cells) in this experiment were CD3+T cells transfected with TCR of the present disclosure specific to the AFP antigen short peptide. The transfected high-affinity TCR molecules were as follows (TCR names specifically used in this example and the following examples, such as TCR1, TCR2, etc. were not the same as the TCR numbers in Table 1 and Table 2 above, and the specific sequence of the α chain variable domain and β chain variable domain shall prevail): TCR1 (α chain variable domain of SEQ ID NO: 11, β chain variable domain of SEQ ID NO: 2), TCR2 (a chain variable domain of SEQ ID NO: 13, β chain variable domain of SEQ ID NO: 2), TCR3 (α chain variable domain of SEQ ID NO: 14, β chain variable domain of SEQ ID NO: 2), TCR4 (α chain variable domain of SEQ ID NO: 15, β chain variable domain of SEQ ID NO: 2), TCR5 (α chain variable domain of SEQ ID NO: 17, β chain variable domain of SEQ ID NO: 2) and TCR6 (α chain variable domain of SEQ ID NO: 18, β chain variable domain of SEQ ID NO: 2). CD3+T cells from the same volunteer transfected with the wild-type TCR corresponding to the high-affinity TCR of the present disclosure (A0B0, α-chain of SEQ ID NO: 28, β-chain of SEQ ID NO: 29), and transfected with other high-affinity TCRs (A6) were used as control groups.

Solution of Short Peptide
The corresponding short peptide was added to the corresponding target cell (T2) assay group, and then serially diluted. The final concentrations of the short peptide were 10-8M-10-13M.

ELISPOT
According to the manufacturer's instructions, the plate was prepared as follows: the anti-human IFN-γ capture antibody was diluted at 1:200 with 10 ml of sterile PBS per plate, and then aliquots of 50 microliters of the diluted capture antibody were added to each well. The plate was incubated overnight at 4° C. After incubation, the plate was washed to remove excess capture antibody. 200 μl/well of PBS medium containing 5% FBS was added, and the plate was incubated at room temperature for 2 hours to block the plate. Then the medium was washed away from the plate, and any remaining wash buffer was removed by tapping the ELISPOT plate on a piece of paper.

Then the assay components were added to the ELISPOT plate in the following order:
100 microliters of target cells 1*10⁵ cells/ml (a total of about 1*10⁴ target cells/well).
100 microliters of effector cells (1*103 effector cells/well and AFP TCR positive T cell/well).
All wells were prepared in duplicate.
Then the plate was incubated overnight (37° C./5% CO₂). The next day, the medium was discarded, the plate was washed twice with double distilled water, then washed for three times with washing buffer, tapped on a piece of paper towel to remove residual washing buffer. Then the detection antibody was diluted at 1:200 with PBS containing 5% FBS, and added to each well at 50 μl/well. The plate was incubated at room temperature for 2 hours, then washed for 3 times with washing buffer, and tapped on a piece of paper towel to remove excess washing buffer.

Streptavidin-alkaline phosphatase was diluted at 1:100 with PBS containing 5% FBS, 50 microliters of diluted streptavidin-alkaline phosphatase was added to each well and the plate was incubated at room temperature for 1 hour. Then the plate was washed for 4 times with washing buffer, washed for 2 times with PBS, and tapped on a piece of paper towel to remove excess washing buffer and PBS. After washing, 50 μl/well of BCIP/NBT solution provided in the kit was added for development. During development, the plate was covered with a tin foil and protected from light, and let it stand for 2-5 minutes. During this period, the spots of the developing plate were routinely checked to determine the best time to stop the reaction. The BCIP/NBT solution was removed and the plate was rinsed with double distilled water to quench the development reaction, and spin-dried. Then the bottom of the well plate was removed, the plate was dried at room temperature until each well was completely dry. And then the immunospot plate counter (CTL, Cellular Technology Limited) was used to count the spots formed on the bottom membrane of the plate.

Results

The ELISPOT experiment (as described above) was used to test the release of IFN-γ from the T cells transduced with the TCR of the present disclosure in response to target cells loaded with AFP antigen short peptide of FMNKFIYEI (SEQ ID NO: 25). Graphpad prism6 was used to plot the number of ELSPOT spots observed in each well.

The results of the experiment were shown in FIGS. 10a, 10b, 10c, 10d, 10e and 10f. The T cells (effector cells) transduced with the TCR of the present disclosure exhibited a good activation response to the target cells loaded with the specific short peptide, and released much higher level of IFN-γ than that of effector cells transduced with wild-type TCR. Meanwhile, the T cells (effector cells) transduced with other TCRs (A6) exhibited substantially no activation response to the corresponding target cells.

Example 10. Activation Assay of the Effector Cells Transfected with the High-Affinity TCR of the Present Disclosure Against Tumor Cell Lines This example demonstrates that effector cells transfected with the high affinity TCR of the present disclosure have a good specific activation effect on target cells.

The function and specificity of the high affinity TCR of the present disclosure in cells were examined by ELISPOT assay. Methods for detecting cellular function using ELISPOT assays were well known to a skilled person in the art. In the IFN-γ ELISPOT assay of this example, CD3+T cells isolated from the blood of healthy volunteers and transfected with the high affinity TCR of the present disclosure were used as effector cells.

The TCRs of the present disclosure were randomly selected, TCR1 (α chain variable domain of SEQ ID NO: 11, β chain variable domain of SEQ ID NO: 2), TCR3 (α chain variable domain of SEQ ID NO: 14, β chain variable domain SEQ ID NO: 2), TCR5 (α chain variable domain of SEQ ID NO: 17, β chain variable domain of SEQ ID NO: 2) and TCR6 (α chain variable domain of SEQ ID NO: 18, β chain variable domain of SEQ ID NO: 2). Effector cells in the control group were labeled as A0B0 (transfected with wild-type TCR, α chain of SEQ ID NO: 28, β chain of SEQ ID NO: 29) and A6 (transfected with other TCR that is not of the present disclosure). The target cell lines were HepG2, HUH-6, Hep3β, HCCC9810 and SNU-398 cells, among which, the target cell line HepG2 expressed relevant antigens and its genotype was also consistent with positive cell lines. HUH-6, Hep3β, HCCC9810 and SNU-398 were negative cell lines and used as controls.

Firstly, a ELISPOT plate was prepared. The ELISPOT plate was activated and coated with ethanol overnight at 4° C. On the first day of the experiment, the coating solution was removed, and the plate was washed, blocked and incubated at room temperature for 2 hrs, and the blocking solution was removed. Components of the assay were added to the ELISPOT plate in the following order: the medium for adjusting effector cells to $1 \times 10^4$ cells/ml, and the medium for adjusting each target cell line to $2 \times 10^5$ cells/ml. After homogeneously mixing, 100 μL of target cell line (i.e., 20,000 cells/well) and 100 μL of effector cells (i.e., 1,000 cells/well) were added to the corresponding wells in duplicate, and incubated overnight (37° C., 5% $CO_2$). On the second day of the experiment, the plate was washed, subjected to a secondary detection and development, and dried, and the spots formed on the film were counted using an immunospot plate reader (ELISPOT READER system; AID20 company).

Figure 11:
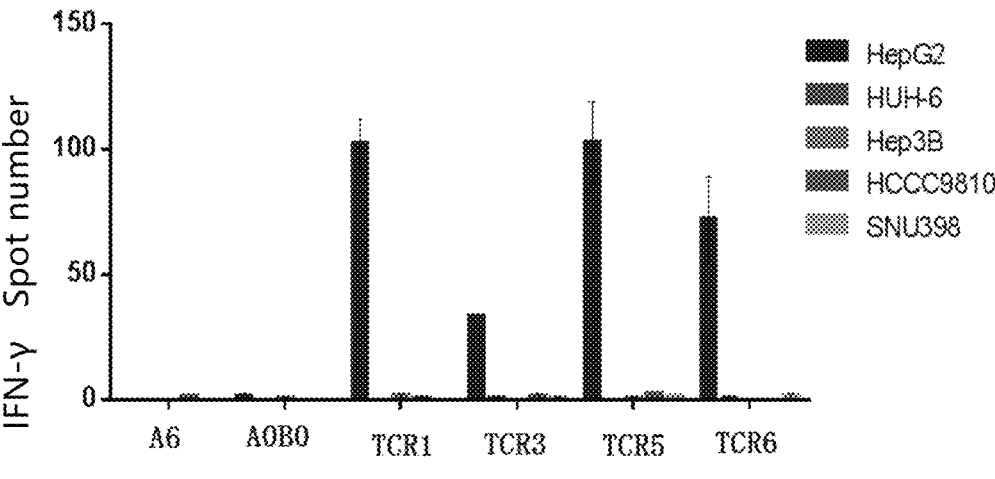
FIG. 11 shows the results of the activation of the effector cells transfected with the high-affinity TCR of the present disclosure against tumor cell lines.

Results were shown in FIG. 11, in which the effector cells transfected with the high affinity TCR of the present disclosure exhibited no activation effects on negative target cells, while exhibited excellent specific activation effects on positive target cells, which were significantly superior to the effector cells transfected with WT TCR.

Example 11. Killing Effects Assay of Effector Cells Transfected with High Affinity TCR of the Present Disclosure In this example, the release of LDH was determined by non-radioactive cytotoxicity assay to verify the killing function of cells transduced with the TCR of the present disclosure. The assay was a colorimetric substitution assay for 51Cr release cytotoxicity assay to quantify lactate dehydrogenase (LDH) released after cell lysis. LDH released in the medium was detected using a 30 minute-coupled enzyme reaction, in which LDH converts tetrazolium salt (INT) into red formazan. The amount of produced red product was directly proportional to the number of lysed cells. Absorbance data of visible light at 490 nm can be collected using a standard 96-well plate reader.

Methods for detecting cellular function using LDH release assay were well known to a skilled person in the art. In the LDH experiment of this example, PBL cells isolated from the blood of healthy volunteers transfected with high affinity TCR of the present disclosure by lentivirus were used as effector cells. The target cell lines were HepG2, HCCC9810 and SNU-398, among which, HepG2 expressed relevant antigens and its genotype was also consistent with positive cell lines; and HCCC9810 and SNU-398 were negative target cell lines as a control.

The target cell lines were transfected with TCR1 (α chain variable domain of SEQ ID NO: 11, β chain variable domain of SEQ ID NO: 2), TCR3 (α chain variable domain of SEQ ID NO: 14, β chain variable domain SEQ ID NO: 2), TCR5 (α chain variable domain of SEQ ID NO: 17, β chain variable domain of SEQ ID NO: 2) and TCR6 (α chain variable domain of SEQ ID NO: 18, β chain variable domain of SEQ ID NO: 2), respectively. Effector cells in the control group were labeled as A6 (transfected with other TCR that was not of the present disclosure).

Firstly, a LDH plate was prepared. On the first day of the experiment, components of the assay were added to the plate in the following order: the medium for adjusting effect cells to $3 \times 10^5$ cells/ml, and the medium for adjusting each target cell line to $3 \times 10^5$ cells/ml. After homogeneously mixing, 100 μL of target cell line (i.e., 30,000 cells/well) and 100 μL of effector cells (i.e., 30,000 cells/well) were added to the corresponding wells in thriplicate. Wells for spontaneous effector cells, for spontaneous target cells, for maximum target cells, for volume-corrected control and for medium background control were simultaneously set, each containing 200 μL of liquid. The plate was incubated overnight (37° C., 5% $CO_2$). On the second day of the experiment, color development was detected, and after the reaction was terminated, the absorbance at 490 nm was recorded using a microplate reader (Bioteck).

Figure 12:
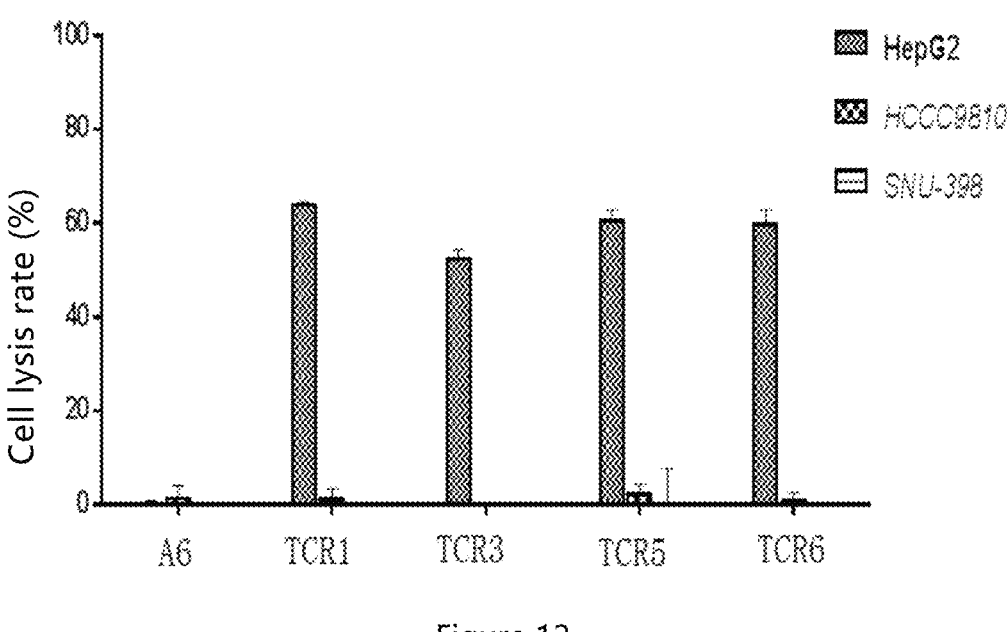
FIG. 12 shows the results of killing effects of the effector cells transfected with the high-affinity TCR of the present disclosure.

Results were shown in FIG. 12, in which the effector cells transfected with the TCR of the present disclosure exhibited strong killing effects on target cells expressing relevant antigens, while substantially exhibited no killing effects on target cells not expressing relevant antigens.

Example 12. In Vivo Efficacy of the High-Affinity TCR Molecule of the Present Disclosure T cells transfected with the high-affinity TCR of the present disclosure were injected into mice as xenotransplantation models of human liver cancer cell, and the inhibitory effects thereof on tumors in vivo were tested.

In the experiment, NSG mice (Beijing Biocytogene Biotechnology Co., Ltd.) (female, experimental age of 6-8 weeks) were used as experimental objects. The mice were subjected to unilateral subcutaneous injection in the abdomen with a suspension of collected and suspended HEPG2 tumor cells (ATCC) at $1*10^7$ cells/mouse (injection volume: 200ul) 20 days before the experiment to establish mice xenotransplantation models of human liver cancer cell.

On the day of the experiment, the long diameter (a) and short diameter (b) of the formed tumor of each mouse were measured with a vernier caliper, and the tumor volume was calculated according to the following formula: $V=a*b^2/2$; and the groups of mice were: the control group (T cells transfected with irrelevant TCR, n=6) labeled as A6, T cell group transfected with TCR1 ($\alpha$ chain variable domain SEQ ID NO: 11, $\beta$ chain variable domain SEQ ID NO: 2, n=6) and T cell group transfected with TCR5 ($\alpha$ chain variable domain SEQ ID NO: 17, $\beta$ chain variable domain SEQ ID NO: 2, n=6). Mice were randomly grouped according to the tumor volume. After the mice were grouped, the prepared T cells were taken and injected into the above grouped mice through tail vein at $2.5*10^7$ cells/mouse, respectively.

After the cells were injected, 100 µl of prepared IL-2 solution (50000IU/100UL) was injected into the intraperitoneal cavity of each mouse, and then the same amount of IL-2 solution was continuously injected every day for the following 4 days. Since the beginning of the experiment, the diameters of tumors in the mice were measured and the tumor volume was calculated every 3 days according to the above method, which continued until the mice were affected by the excessive tumor or the tumor regressed. The above data were sorted and the tumor volume of each group of mice was statistically analyzed.

Figure 13:
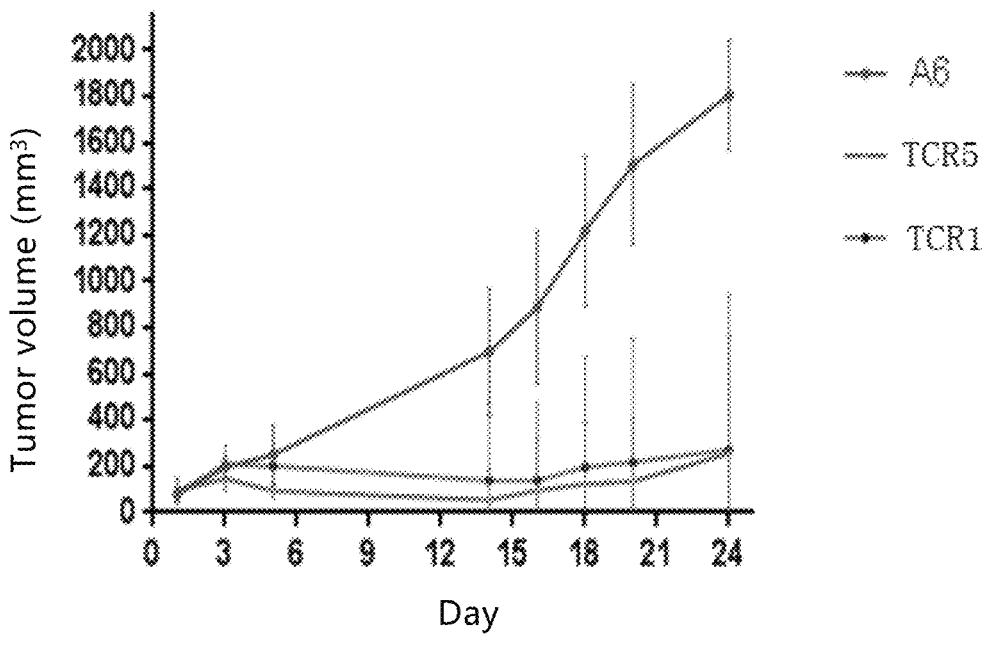
FIG. 13 shows the results of in vivo efficacy of the T cells transfected with the high-affinity TCR of the present disclosure.

The obtained experimental results were shown in FIG. 13. In the group of mice injected with T cells transfected with the high-affinity TCR of the present disclosure, the growth of tumors was obviously inhibited and exhibited a shrinking trend. While the tumor volume of mice injected with T cells transfected with irrelevant TCR still increased rapidly.

Each reference provided herein is incorporated by reference to the same extent as if each reference was individually incorporated by reference. In addition, it should be understood that based on the above teaching content of the disclosure, those skilled in the art can practice various changes or modifications to the disclosure, and these equivalent forms also fall within the scope of the appended claims.

We claim:

1. A T cell receptor (TCR), wherein the T cell receptor has an activity of binding FMNKFIYEI(SEQ ID NO: 33)-HLA A0201 complex, and the T cell receptor comprises a TCRα chain variable domain and a TCRβ chain variable domain, wherein the TCRα chain variable domain comprises 3 CDR regions, which are CDR1α, CDR2α and CDR3α, and the TCRβ chain variable domain comprises 3 CDR regions, which are CDR1β, CDR2β and CDR3β, wherein the CDR1α, CDR2α, CDR3α, CDR1β, CDR2β and CDR3β of the TCR are shown in the following CDR NO: 1, 3, 6, 7, 9, 10, 12 or 13

| CDR No. | CDR1α | CDR2α | CDR3α |
|---|---|---|---|
| 1 | DSAIYN (SEQ ID NO: 34) | IQSSQRE (SEQ ID NO: 35) | AVDSGGSNYKLT (SEQ ID NO: 53) |
| 3 | DSAIYN (SEQ ID NO: 34) | IQSSQRE (SEQ ID NO: 35) | AVDGADSNYKLT (SEQ ID NO: 41) |
| 6 | DSAIYN (SEQ ID NO: 34) | IQSSQRE (SEQ ID NO: 35) | AVDSHPSNYKLT (SEQ ID NO: 44) |
| 7 | DSAIYN (SEQ ID NO: 34) | IQSSQRE (SEQ ID NO: 35) | AVDAAQSNYKLT (SEQ ID NO: 45) |
| 9 | DSAIYN (SEQ ID NO: 34) | IQSSQRE (SEQ ID NO: 35) | AVDWHPSNYKLT (SEQ ID NO: 47) |
| 10 | DSAIYN (SEQ ID NO: 34) | IQSSQRE (SEQ ID NO: 35) | AVDSQDSNYKLT (SEQ ID NO: 48) |
| 12 | DSAIYN (SEQ ID NO: 34) | IQSSQRE (SEQ ID NO: 35) | AVDTMDSNYKLT (SEQ ID NO: 50) |
| 13 | DSAIYN (SEQ ID NO: 34) | IQSSQRE (SEQ ID NO: 35) | AVDHHPSNYKLT (SEQ ID NO: 51) |

| CDR No. | CDR1β | CDR2β | CDR3β |
|---|---|---|---|
| 1 | SGHVS (SEQ ID NO: 37) | FQNEAQ (SEQ ID NO: 38) | ASSLFGQGREKLF (SEQ ID NO: 39) |
| 3 | SGHVS (SEQ ID NO: 37) | FQNEAQ (SEQ ID NO: 38) | ASSLFGQGREKLF (SEQ ID NO: 39) |
| 6 | SGHVS (SEQ ID NO: 37) | FQNEAQ (SEQ ID NO: 38) | ASSLFGQGREKLF (SEQ ID NO: 39) |
| 7 | SGHVS (SEQ ID NO: 37) | FQNEAQ (SEQ ID NO: 38) | ASSLFGQGREKLF (SEQ ID NO: 39) |
| 9 | SGHVS (SEQ ID NO: 37) | FQNEAQ (SEQ ID NO: 38) | ASSLFGQGREKLF (SEQ ID NO: 39) |
| 10 | SGHVS (SEQ ID NO: 37) | FQNEAQ (SEQ ID NO: 38) | ASSLFGQGREKLF (SEQ ID NO: 39) |
| 12 | SGHVS (SEQ ID NO: 37) | FQNEAQ (SEQ ID NO: 38) | ASSLFGQGREKLF (SEQ ID NO: 39) |
| 13 | SGHVS (SEQ ID NO: 37) | FQNEAQ (SEQ ID NO: 38) | ASSLFGQGREKLF (SEQ ID NO: 39). |

2. The TCR of claim 1, wherein the β-chain variable domain of the TCR is an amino acid sequence having at least 90%, 91%, 92%, 93%, 94%, 95%, 96%, 97%, 98%, 99% or 100% sequence homology with the amino acid sequence of SEQ ID NO: 2.

3. The TCR of claim 1, wherein the affinity of the TCR for FMNKFIYEI(SEQ ID NO: 33)-HLA A0201 complex is at least 5 times of that of a wild type TCR.

4. The TCR of claim 1, wherein the α-chain variable domain of the TCR comprises an amino acid sequence having at least 90%, 91%, 92%, 93%, 94%, 95%, 96%, 97%, 98% or 99% sequence homology with the amino acid sequence of SEQ ID NO: 1.

5. The TCR of claim 1, wherein, the TCRβ chain variable domain is an amino acid sequence of SEQ ID NO: 2.

6. The TCR of claim 1, wherein:
   the TCR is soluble; and/or
   the TCR is a single-chain TCR; and/or
   a conjugate binds to the α chain and/or β chain of the TCR at C- or N-terminal.

7. The TCR of claim 1, wherein, the TCR is an αβ heterodimeric TCR comprising α chain constant region sequence TRAC and β chain constant region sequence TRBC1 or TRBC2.

8. The TCR of claim 1, wherein the TCR comprises (i) all or part of the TCRα chain except for its transmembrane domain, and (ii) all or part of the TCR β chain except for its transmembrane domain, wherein both of (i) and (ii) comprise the variable domain and at least a portion of the constant domain of the TCR chain.

9. The TCR of claim 7, wherein an artificial inter-chain disulfide bond is contained between the α chain constant region and the γ chain constant region of the TCR.

10. The TCR of claim 9, wherein cysteine residues forming the artificial inter-chain disulfide bond between the constant regions of the TCRα and β-chains are substituted for one or more combinations of sites selected from the group consisting of:
   Thr48 in exon 1 of TRAC*01 and Ser57 in exon 1 of TRBC2*01 or TRBC1*01;

Thr45 in exon 1 of TRAC*01 and Ser77 in exon 1 of TRBC2*01 or TRBC1*01;

Tyr10 in exon 1 of TRAC*01 and Ser17 in exon 1 of TRBC2*01 or TRBC1*01;

Thr45 in exon 1 of TRAC*01 and Asp59 in exon 1 of TRBC2*01 or TRBC1*01;

Ser15 in exon 1 of TRAC*01 and Glu15 in exon 1 of TRBC2*01 or TRBC1*01;

Arg53 in exon 1 of TRAC*01 and Ser54 in exon 1 of TRBC2*01 or TRBC1*01;

Pro89 in exon 1 of TRAC*01 and Ala19 in exon 1 of TRBC2*01 or TRBC1*01; and

Tyr10 in exon 1 of TRAC*01 and Glu20 in exon 1 of TRBC2*01 or TRBC1*01.

11. The TCR of claim 1, wherein, the amino acid sequence of the α-chain variable domain of the TCR is selected from the group consisting of: SEQ ID NOs: 11, 13, 16, 17, 19, 20, 22, and 23; and the amino acid sequence of the β-chain variable domain of the TCR is SEQ ID NO: 2.

12. The TCR of claim 6, wherein, the TCR is a single-chain TCR consisting of an α-chain variable domain and a β-chain variable domain, and the α-chain variable domain and the β-chain variable domain are linked by linker which is a flexible short peptide sequence.

13. The TCR of claim 6, wherein the conjugate that binds to the TCR is a detectable label, a therapeutic agent, a PK modified moiety, or any combination thereof.

14. The TCR of claim 13, wherein the therapeutic agent that binds to the TCR is an anti-CD3 antibody linked to the α or β chain of the TCR at C- or N-terminal.

15. A multivalent TCR complex comprising at least two TCR molecules, and at least one TCR molecule is the TCR of claim 1.

16. A nucleic acid molecule encoding the TCR of claim 1.

17. A vector comprising the nucleic acid molecule of claim 16.

18. A cell expressing the vector of claim 17.

19. A pharmaceutical composition, comprising a pharmaceutically acceptable carrier, and the TCR of claim 1, a multivalent TCR complex or an isolated cell expressing the TCR; wherein the multivalent TCR complex comprises at least two TCR molecules, and at least one TCR molecule is the TCR of claim 1.

* * * * *

SEQUENCE LISTING

```
<160> NUMBER OF SEQ ID NOS: 53

<210> SEQ ID NO 1
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 1

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asn Ser Gly Gly
                85                  90                  95

Ser Asn Tyr Lys Leu Thr Phe Gly Lys Gly Thr Leu Leu Thr Val Asn
            100                 105                 110

Pro

<210> SEQ ID NO 2
<211> LENGTH: 115
<212> TYPE: PRT
<213> ORGANISM: Artificial sequence
<220> FEATURE:
<223> OTHER INFORMATION: Synthetic polypeptide
```

```
<400> SEQUENCE: 2

Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
                20                  25                  30

Phe Trp Tyr Gln Gln Ala Leu Gly Gln Gly Pro Glu Phe Leu Thr Tyr
            35                  40                  45

Phe Gln Asn Glu Ala Gln Leu Asp Lys Ser Gly Leu Pro Ser Asp Arg
        50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Leu
                85                  90                  95

Phe Gly Gln Gly Arg Glu Lys Leu Phe Phe Gly Ser Gly Thr Gln Leu
            100                 105                 110

Ser Val Leu
        115

<210> SEQ ID NO 3
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 3

Lys Gln Glu Val Thr Gln Ser Pro Ala Ser Leu Ser Val Pro Glu Gly
1               5                   10                  15

Glu Asn Val Ser Ile Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Glu Asp Val
65                  70                  75                  80

Gln Pro Gly Asp Ser Ala Thr Tyr Leu Cys Ala Val Asn Ser Gly Gly
                85                  90                  95

Ser Asn Tyr Lys Leu Thr Phe Gly Lys Gly Thr Lys Leu Thr Val Asn
            100                 105                 110

Pro

<210> SEQ ID NO 4
<211> LENGTH: 115
<212> TYPE: PRT
<213> ORGANISM: Artificial sequence
<220> FEATURE:
<223> OTHER INFORMATION: Synthetic polypeptide

<400> SEQUENCE: 4

Gly Ala Gly Val Ser Gln Ser Pro Arg Tyr Leu Ser Val Lys Arg Gly
1               5                   10                  15

Gln Asp Val Thr Leu Arg Cys Asp Pro Ile Ser Gly His Val Ser Leu
                20                  25                  30

Phe Trp Tyr Gln Gln Ala Pro Gly Gln Gly Pro Glu Phe Leu Thr Tyr
            35                  40                  45

Phe Gln Asn Glu Ala Gln Leu Asp Lys Ser Gly Leu Pro Ser Asp Arg
```

-continued

```
        50              55              60

Phe Phe Ala Glu Arg Pro Glu Gly Ser Val Ser Thr Leu Lys Ile Gln
65                  70                  75                  80

Arg Val Gln Pro Glu Asp Ser Ala Val Tyr Leu Cys Ala Ser Ser Leu
                85                  90                  95

Phe Gly Gln Gly Arg Glu Lys Leu Phe Phe Gly Ser Gly Thr Gln Leu
            100                 105                 110

Ser Val Asp
        115

<210> SEQ ID NO 5
<211> LENGTH: 339
<212> TYPE: DNA
<213> ORGANISM: Artificial sequence
<220> FEATURE:
<223> OTHER INFORMATION: Synthetic polynucleotides

<400> SEQUENCE: 5
aaacaagaag ttactcaaag cccggcgagc ctgagcgtgc cggagggtga aaacgttagc      60
atcaactgca gcttcaccga cagcgcgatt tacaacctgc aatggtttcg tcaggacccg     120
ggcaagggcc tgaccagcct gctgctgatc cagagcagcc aacgtgagca gaccagcggt     180
cgtctgaacg cgagcctgga caaaagcagc ggccgtagca ccctgtatat tgaagacgtg     240
caaccgggtg atagcgcgac ctacctgtgc gcggttaaca gcggtggcag caactataag     300
ctgacctttg gcaagggcac caaactgacc gttaacccg                            339

<210> SEQ ID NO 6
<211> LENGTH: 345
<212> TYPE: DNA
<213> ORGANISM: Artificial sequence
<220> FEATURE:
<223> OTHER INFORMATION: Synthetic polynucleotides

<400> SEQUENCE: 6
ggcgcgggtg tgagccaaag cccgcgttac ctgagcgtga aacgtggtca ggacgttacc      60
ctgcgttgcg atccgatcag cggccacgtt agcctgttct ggtatcagca agcgccgggt     120
cagggtccgg agttcctgac ctattttcaa aacgaagcgc agctggacaa gagcggtctg     180
ccgagcgatc gtttctttgc ggagcgtccg gaaggcagcg tgagcaccct gaaaattcaa     240
cgtgtgcagc cggaggacag cgcggtttat ctgtgcgcga gcagcctgtt tggtcaaggc     300
cgtgaaaaac tgttctttgg tagcggcacc cagctgagcg ttgat                    345

<210> SEQ ID NO 7
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 7

Gly Gly Gly Ser Glu Gly Gly Gly Ser Glu Gly Gly Gly Ser Glu Gly
1               5                   10                  15

Gly Gly Ser Glu Gly Gly Thr Gly
            20

<210> SEQ ID NO 8
<211> LENGTH: 72
<212> TYPE: DNA
<213> ORGANISM: Artificial sequence
```

```
<220> FEATURE:
<223> OTHER INFORMATION: Synthetic polynucleotides

<400> SEQUENCE: 8
ggtggcggta gcgagggcgg tggcagcgaa ggtggcggta gcgagggcgg tggcagcgaa      60
ggtggcaccg gt                                                         72

<210> SEQ ID NO 9
<211> LENGTH: 252
<212> TYPE: PRT
<213> ORGANISM: Artificial sequence
<220> FEATURE:
<223> OTHER INFORMATION: Synthetic polypeptide

<400> SEQUENCE: 9

Lys Gln Glu Val Thr Gln Ser Pro Ala Ser Leu Ser Val Pro Glu Gly
1               5                   10                  15

Glu Asn Val Ser Ile Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Glu Asp Val
65                  70                  75                  80

Gln Pro Gly Asp Ser Ala Thr Tyr Leu Cys Ala Val Asn Ser Gly Gly
                85                  90                  95

Ser Asn Tyr Lys Leu Thr Phe Gly Lys Gly Thr Lys Leu Thr Val Asn
                100                 105                 110

Pro Gly Gly Gly Ser Glu Gly Gly Gly Ser Glu Gly Gly Gly Ser Glu
            115                 120                 125

Gly Gly Gly Ser Glu Gly Gly Thr Gly Gly Ala Gly Val Ser Gln Ser
        130                 135                 140

Pro Arg Tyr Leu Ser Val Lys Arg Gly Gln Asp Val Thr Leu Arg Cys
145                 150                 155                 160

Asp Pro Ile Ser Gly His Val Ser Leu Phe Trp Tyr Gln Gln Ala Pro
                165                 170                 175

Gly Gln Gly Pro Glu Phe Leu Thr Tyr Phe Gln Asn Glu Ala Gln Leu
                180                 185                 190

Asp Lys Ser Gly Leu Pro Ser Asp Arg Phe Phe Ala Glu Arg Pro Glu
            195                 200                 205

Gly Ser Val Ser Thr Leu Lys Ile Gln Arg Val Gln Pro Glu Asp Ser
        210                 215                 220

Ala Val Tyr Leu Cys Ala Ser Ser Leu Phe Gly Gln Gly Arg Glu Lys
225                 230                 235                 240

Leu Phe Phe Gly Ser Gly Thr Gln Leu Ser Val Asp
                245                 250

<210> SEQ ID NO 10
<211> LENGTH: 756
<212> TYPE: DNA
<213> ORGANISM: Artificial sequence
<220> FEATURE:
<223> OTHER INFORMATION: Synthetic polynucleotides

<400> SEQUENCE: 10
aaacaagaag ttactcaaag cccggcgagc ctgagcgtgc cggagggtga aaacgttagc      60
```

-continued

```
atcaactgca gcttcaccga cagcgcgatt tacaacctgc aatggtttcg tcaggacccg      120
ggcaagggcc tgaccagcct gctgctgatc cagagcagcc aacgtgagca gaccagcggt      180
cgtctgaacg cgagcctgga caaaagcagc ggccgtagca ccctgtatat tgaagacgtg      240
caaccgggtg atagcgcgac ctacctgtgc gcggttaaca gcggtggcag caactataag      300
ctgacctttg gcaagggcac caaactgacc gttaacccgg gtggcggtag cgagggcggt      360
ggcagcgaag gtggcggtag cgagggcggt ggcagcgaag gtggcaccgg tggcgcgggt      420
gtgagccaaa gcccgcgtta cctgagcgtg aaacgtggtc aggacgttac cctgcgttgc      480
gatccgatca gcggccacgt tagcctgttc tggtatcagc aagcgccggg tcagggtccg      540
gagttcctga cctattttca aaacgaagcg cagctggaca gagcggtct gccgagcgat       600 cgtttctttg cggagcgtcc ggaaggcagc gtgagcaccc tgaaaattca acgtgtgcag      660
ccggaggaca gcgcggttta tctgtgcgcg agcagcctgt ttggtcaagg ccgtgaaaaa      720
ctgttctttg gtagcggcac ccagctgagc gttgat                                756
```

```
<210> SEQ ID NO 11
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 11

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asp Ser Gly Gly
                85                  90                  95

Ser Asn Tyr Lys Leu Thr Phe Gly Lys Gly Thr Leu Leu Thr Val Asn
            100                 105                 110

Pro
```

```
<210> SEQ ID NO 12
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 12

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60
```

-continued

```
Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Glu Asp Gln Gly
                85                  90                  95

Ser Asn Tyr Lys Leu Thr Phe Gly Lys Gly Thr Leu Leu Thr Val Asn
            100                 105                 110

Pro
```

```
<210> SEQ ID NO 13
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 13

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asp Gly Ala Asp
                85                  90                  95

Ser Asn Tyr Lys Leu Thr Phe Gly Lys Gly Thr Leu Leu Thr Val Asn
            100                 105                 110

Pro
```

```
<210> SEQ ID NO 14
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 14

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asn Ser Val Arg
                85                  90                  95

Gly Gly Tyr Lys Leu Thr Phe Gly Lys Gly Thr Leu Leu Thr Val Asn
            100                 105                 110

Pro
```

```
<210> SEQ ID NO 15
```

```
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 15

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Glu Gly Ala Arg
                85                  90                  95

Ser Asn Tyr Lys Leu Thr Phe Gly Lys Gly Thr Leu Leu Thr Val Asn
                100                 105                 110

Pro

<210> SEQ ID NO 16
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 16

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asp Ser His Pro
                85                  90                  95

Ser Asn Tyr Lys Leu Thr Phe Gly Lys Gly Thr Leu Leu Thr Val Asn
                100                 105                 110

Pro

<210> SEQ ID NO 17
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 17

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30
```

-continued

```
Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asp Ala Ala Gln
            85                  90                  95

Ser Asn Tyr Lys Leu Thr Phe Gly Lys Gly Thr Leu Leu Thr Val Asn
            100                 105                 110

Pro

<210> SEQ ID NO 18
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 18

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asn Ser Trp Thr
            85                  90                  95

Gly Gly Tyr Lys Leu Thr Phe Gly Lys Gly Thr Leu Leu Thr Val Asn
            100                 105                 110

Pro

<210> SEQ ID NO 19
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 19

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asp Trp His Pro
            85                  90                  95
```

-continued

```
Ser Asn Tyr Lys Leu Thr Phe Gly Lys Gly Thr Leu Leu Thr Val Asn
            100                 105                 110

Pro

<210> SEQ ID NO 20
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 20

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asp Ser Gln Asp
            85                  90                  95

Ser Asn Tyr Lys Leu Thr Phe Gly Lys Gly Thr Leu Leu Thr Val Asn
            100                 105                 110

Pro

<210> SEQ ID NO 21
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 21

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asn Ser Tyr Tyr
            85                  90                  95

Asp Gly Tyr Lys Leu Thr Phe Gly Lys Gly Thr Leu Leu Thr Val Asn
            100                 105                 110

Pro

<210> SEQ ID NO 22
<211> LENGTH: 113
<212> TYPE: PRT
<213> ORGANISM: Artificial sequence
<220> FEATURE:
<223> OTHER INFORMATION: Synthetic polypeptide
```

<400> SEQUENCE: 22

```
Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asp Thr Met Asp
                85                  90                  95

Ser Asn Tyr Lys Leu Thr Phe Gly Lys Gly Thr Leu Leu Thr Val Asn
            100                 105                 110

Pro
```

<210> SEQ ID NO 23
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 23

```
Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asp His His Pro
                85                  90                  95

Ser Asn Tyr Lys Leu Thr Phe Gly Lys Gly Thr Leu Leu Thr Val Asn
            100                 105                 110

Pro
```

<210> SEQ ID NO 24
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 24

```
Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60
```

-continued

```
Ser Leu Asp Lys Ser Ser Gly Arg Ser Thr Leu Tyr Ile Ala Ala Ser
65              70              75              80

Gln Pro Gly Asp Ser Ala Thr Tyr Leu Cys Ala Val Asn Ser Ile Tyr
                85              90              95

Gly Asp Tyr Lys Leu Thr Phe Gly Lys Gly Thr Leu Leu Thr Val Asn
            100             105             110

Pro

<210> SEQ ID NO 25
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 25

Phe Met Asn Lys Phe Ile Tyr Glu Ile
1               5

<210> SEQ ID NO 26
<211> LENGTH: 207
<212> TYPE: PRT
<213> ORGANISM: Artificial sequence
<220> FEATURE:
<223> OTHER INFORMATION: Synthetic polypeptide

<400> SEQUENCE: 26

Lys Gln Glu Val Thr Gln Ile Pro Ala Ala Leu Ser Val Pro Glu Gly
1               5               10              15

Glu Asn Leu Val Leu Asn Cys Ser Phe Thr Asp Ser Ala Ile Tyr Asn
                20              25              30

Leu Gln Trp Phe Arg Gln Asp Pro Gly Lys Gly Leu Thr Ser Leu Leu
            35              40              45

Leu Ile Gln Ser Ser Gln Arg Glu Gln Thr Ser Gly Arg Leu Asn Ala
        50              55              60

Ser Leu Asp Lys Ser Ser Gly Arg Ser Thr Leu Tyr Ile Ala Ala Ser
65              70              75              80

Gln Pro Gly Asp Ser Ala Thr Tyr Leu Cys Ala Val Asn Ser Gly Gly
                85              90              95

Ser Asn Tyr Lys Leu Thr Phe Gly Lys Gly Thr Leu Leu Thr Val Asn
            100             105             110

Pro Asn Ile Gln Asn Pro Asp Pro Ala Val Tyr Gln Leu Arg Asp Ser
            115             120             125

Lys Ser Ser Asp Lys Ser Val Cys Leu Phe Thr Asp Phe Asp Ser Gln
        130             135             140

Thr Asn Val Ser Gln Ser Lys Asp Ser Asp Val Tyr Ile Thr Asp Lys
145             150             155             160

Cys Val Leu Asp Met Arg Ser Met Asp Phe Lys Ser Asn Ser Ala Val
            165             170             175

Ala Trp Ser Asn Lys Ser Asp Phe Ala Cys Ala Asn Ala Phe Asn Asn
            180             185             190

Ser Ile Ile Pro Glu Asp Thr Phe Phe Pro Ser Pro Glu Ser Ser
        195             200             205

<210> SEQ ID NO 27
<211> LENGTH: 245
<212> TYPE: PRT
<213> ORGANISM: Artificial sequence
```

```
<220> FEATURE:
<223> OTHER INFORMATION: Synthetic polypeptide

<400> SEQUENCE: 27

Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
            20                  25                  30

Phe Trp Tyr Gln Gln Ala Leu Gly Gln Gly Pro Glu Phe Leu Thr Tyr
        35                  40                  45

Phe Gln Asn Glu Ala Gln Leu Asp Lys Ser Gly Leu Pro Ser Asp Arg
    50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Leu
                85                  90                  95

Phe Gly Gln Gly Arg Glu Lys Leu Phe Phe Gly Ser Gly Thr Gln Leu
            100                 105                 110

Ser Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
            195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 28
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 28

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asn Ser Gly Gly
```

-continued

```
                   85                  90                  95
Ser Asn Tyr Lys Leu Thr Phe Gly Lys Gly Thr Leu Leu Thr Val Asn
            100                 105                 110

Pro Asn Ile Gln Asn Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
            130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser Cys
            195                 200                 205

Asp Val Lys Leu Val Glu Lys Ser Phe Glu Thr Asp Thr Asn Leu Asn
            210                 215                 220

Phe Gln Asn Leu Ser Val Ile Gly Phe Arg Ile Leu Leu Leu Lys Val
225                 230                 235                 240

Ala Gly Phe Asn Leu Leu Met Thr Leu Arg Leu Trp Ser Ser
                245                 250
```

```
<210> SEQ ID NO 29
<211> LENGTH: 292
<212> TYPE: PRT
<213> ORGANISM: Artificial sequence
<220> FEATURE:
<223> OTHER INFORMATION: Synthetic polypeptide

<400> SEQUENCE: 29

Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
            20                  25                  30

Phe Trp Tyr Gln Gln Ala Leu Gly Gln Gly Pro Glu Phe Leu Thr Tyr
        35                  40                  45

Phe Gln Asn Glu Ala Gln Leu Asp Lys Ser Gly Leu Pro Ser Asp Arg
        50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Leu
                85                  90                  95

Phe Gly Gln Gly Arg Glu Lys Leu Phe Phe Gly Ser Gly Thr Gln Leu
            100                 105                 110

Ser Val Leu Glu Asp Leu Asn Lys Val Phe Pro Pro Glu Val Ala Val
            115                 120                 125

Phe Glu Pro Ser Glu Ala Glu Ile Ser His Thr Gln Lys Ala Thr Leu
            130                 135                 140

Val Cys Leu Ala Thr Gly Phe Phe Pro Asp His Val Glu Leu Ser Trp
145                 150                 155                 160

Trp Val Asn Gly Lys Glu Val His Ser Gly Val Ser Thr Asp Pro Gln
                165                 170                 175

Pro Leu Lys Glu Gln Pro Ala Leu Asn Asp Ser Arg Tyr Cys Leu Ser
            180                 185                 190

Ser Arg Leu Arg Val Ser Ala Thr Phe Trp Gln Asn Pro Arg Asn His
```

-continued

```
         195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp Cys Gly Phe Thr Ser Val Ser Tyr Gln Gln Gly
                245                 250                 255

Val Leu Ser Ala Thr Ile Leu Tyr Glu Ile Leu Leu Gly Lys Ala Thr
                260                 265                 270

Leu Tyr Ala Val Leu Val Ser Ala Leu Val Leu Met Ala Met Val Lys
        275                 280                 285

Arg Lys Asp Phe
    290
```

```
<210> SEQ ID NO 30
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 30

Gly Gly Gly Gly Ser
1               5

<210> SEQ ID NO 31
<211> LENGTH: 6
<212> TYPE: DNA
<213> ORGANISM: Artificial sequence
<220> FEATURE:
<223> OTHER INFORMATION: Synthetic polynucleotides

<400> SEQUENCE: 31 ccatgg                                                          6

<210> SEQ ID NO 32
<211> LENGTH: 8
<212> TYPE: DNA
<213> ORGANISM: Artificial sequence
<220> FEATURE:
<223> OTHER INFORMATION: Synthetic polynucleotides

<400> SEQUENCE: 32 gcggccgc                                                        8

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Phe Met Asn Lys Phe Ile Tyr Glu Ile
1               5

<210> SEQ ID NO 34
<211> LENGTH: 6
<212> TYPE: PRT
<213> ORGANISM: Artificial Sequence
<220> FEATURE:
<223> OTHER INFORMATION: synthetic

<400> SEQUENCE: 34
```

Asp Ser Ala Ile Tyr Asn
1               5

<210> SEQ ID NO 35
<211> LENGTH: 7
<212> TYPE: PRT
<213> ORGANISM: Artificial Sequence
<220> FEATURE:
<223> OTHER INFORMATION: synthetic

<400> SEQUENCE: 35

Ile Gln Ser Ser Gln Arg Glu
1               5

<210> SEQ ID NO 36
<211> LENGTH: 12
<212> TYPE: PRT
<213> ORGANISM: Artificial Sequence
<220> FEATURE:
<223> OTHER INFORMATION: synthetic

<400> SEQUENCE: 36

Ala Val Asn Ser Gly Gly Ser Asn Tyr Lys Leu Thr
1               5                   10

<210> SEQ ID NO 37
<211> LENGTH: 5
<212> TYPE: PRT
<213> ORGANISM: Artificial Sequence
<220> FEATURE:
<223> OTHER INFORMATION: synthetic

<400> SEQUENCE: 37

Ser Gly His Val Ser
1               5

<210> SEQ ID NO 38
<211> LENGTH: 6
<212> TYPE: PRT
<213> ORGANISM: Artificial Sequence
<220> FEATURE:
<223> OTHER INFORMATION: synthetic

<400> SEQUENCE: 38

Phe Gln Asn Glu Ala Gln
1               5

<210> SEQ ID NO 39
<211> LENGTH: 13
<212> TYPE: PRT
<213> ORGANISM: Artificial Sequence
<220> FEATURE:
<223> OTHER INFORMATION: synthetic

<400> SEQUENCE: 39

Ala Ser Ser Leu Phe Gly Gln Gly Arg Glu Lys Leu Phe
1               5                   10

<210> SEQ ID NO 40
<211> LENGTH: 12
<212> TYPE: PRT
<213> ORGANISM: Artificial Sequence
<220> FEATURE:
<223> OTHER INFORMATION: synthetic

<400> SEQUENCE: 40

```
Ala Val Glu Asp Gln Gly Ser Asn Tyr Lys Leu Thr
1               5                   10

<210> SEQ ID NO 41
<211> LENGTH: 12
<212> TYPE: PRT
<213> ORGANISM: Artificial Sequence
<220> FEATURE:
<223> OTHER INFORMATION: synthetic

<400> SEQUENCE: 41

Ala Val Asp Gly Ala Asp Ser Asn Tyr Lys Leu Thr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: synthetic

<400> SEQUENCE: 42

Ala Val Asn Ser Val Arg Gly Gly Tyr Lys Leu Thr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: synthetic

<400> SEQUENCE: 43

Ala Val Glu Gly Ala Arg Ser Asn Tyr Lys Leu Thr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: synthetic

<400> SEQUENCE: 44

Ala Val Asp Ser His Pro Ser Asn Tyr Lys Leu Thr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: synthetic

<400> SEQUENCE: 45

Ala Val Asp Ala Ala Gln Ser Asn Tyr Lys Leu Thr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: synthetic

<400> SEQUENCE: 46

Ala Val Asn Ser Trp Thr Gly Gly Tyr Lys Leu Thr
```

-continued

```
1               5                       10

<210> SEQ ID NO 47
<211> LENGTH: 12
<212> TYPE: PRT
<213> ORGANISM: Artificial Sequence
<220> FEATURE:
<223> OTHER INFORMATION: synthetic

<400> SEQUENCE: 47

Ala Val Asp Trp His Pro Ser Asn Tyr Lys Leu Thr
1               5                       10

<210> SEQ ID NO 48
<211> LENGTH: 12
<212> TYPE: PRT
<213> ORGANISM: Artificial Sequence
<220> FEATURE:
<223> OTHER INFORMATION: synthetic

<400> SEQUENCE: 48

Ala Val Asp Ser Gln Asp Ser Asn Tyr Lys Leu Thr
1               5                       10

<210> SEQ ID NO 49
<211> LENGTH: 12
<212> TYPE: PRT
<213> ORGANISM: Artificial Sequence
<220> FEATURE:
<223> OTHER INFORMATION: synthetic

<400> SEQUENCE: 49

Ala Val Asn Ser Tyr Tyr Asp Gly Tyr Lys Leu Thr
1               5                       10

<210> SEQ ID NO 50
<211> LENGTH: 12
<212> TYPE: PRT
<213> ORGANISM: Artificial Sequence
<220> FEATURE:
<223> OTHER INFORMATION: synthetic

<400> SEQUENCE: 50

Ala Val Asp Thr Met Asp Ser Asn Tyr Lys Leu Thr
1               5                       10

<210> SEQ ID NO 51
<211> LENGTH: 12
<212> TYPE: PRT
<213> ORGANISM: Artificial Sequence
<220> FEATURE:
<223> OTHER INFORMATION: synthetic

<400> SEQUENCE: 51

Ala Val Asp His His Pro Ser Asn Tyr Lys Leu Thr
1               5                       10

<210> SEQ ID NO 52
<211> LENGTH: 12
<212> TYPE: PRT
<213> ORGANISM: Artificial Sequence
<220> FEATURE:
<223> OTHER INFORMATION: synthetic

<400> SEQUENCE: 52

Ala Val Asn Ser Ile Tyr Gly Asp Tyr Lys Leu Thr
1               5                       10
```

-continued

```
<210> SEQ ID NO 53
<211> LENGTH: 12
<212> TYPE: PRT
<213> ORGANISM: Artificial Sequence
<220> FEATURE:
<223> OTHER INFORMATION: Synthetic

<400> SEQUENCE: 53

Ala Val Asp Ser Gly Gly Ser Asn Tyr Lys Leu Thr
1               5                   10
```